(12) United States Patent
Eber et al.

(10) Patent No.: US 10,517,827 B2
(45) Date of Patent: Dec. 31, 2019

(54) DRY POWDER COMPOSITION COMPRISING LONG-CHAIN RNA

(71) Applicant: CureVac AG, Tübingen (DE)

(72) Inventors: Fabian Johannes Eber, Stuttgart (DE); Benyamin Yazdan Panah, Tübingen (DE); Stefanie Sewig, Tübingen (DE); Thomas Ketterer, Gomaringen (DE); Thorsten Mutzke, Reutlingen (DE); Tilmann Roos, Kusterdingen (DE); Michael Sonntag, Tübingen (DE); Michael Wiggenhorn, München (DE); Katharina Kolland, Augsburg (DE)

(73) Assignee: CureVac AG, Tübingen (DE)

( * ) Notice: Subject to any disclaimer, the term of this patent is extended or adjusted under 35 U.S.C. 154(b) by 0 days.

(21) Appl. No.: 15/575,284

(22) PCT Filed: May 20, 2016

(86) PCT No.: PCT/EP2016/000842
§ 371 (c)(1),
(2) Date: Nov. 17, 2017

(87) PCT Pub. No.: WO2016/184575
PCT Pub. Date: Nov. 24, 2016

(65) Prior Publication Data
US 2018/0147146 A1    May 31, 2018

(30) Foreign Application Priority Data

May 20, 2015   (EP) .................................. 15001517
Oct. 13, 2015  (WO) .................. PCT/EP2015/002019

(51) Int. Cl.
```
C07H 21/04      (2006.01)
A61K 9/16       (2006.01)
A61K 48/00      (2006.01)
A61P 31/00      (2006.01)
A61P 31/12      (2006.01)
A61P 37/06      (2006.01)
A61P 37/08      (2006.01)
A61P 31/04      (2006.01)
A61P 33/02      (2006.01)
A61P 35/00      (2006.01)
A61K 39/145     (2006.01)
A61K 39/00      (2006.01)
```
(52) U.S. Cl.
CPC ............ *A61K 9/16* (2013.01); *A61K 9/1682* (2013.01); *A61K 39/145* (2013.01); *A61K 48/005* (2013.01); *A61K 48/0091* (2013.01); *A61P 31/00* (2018.01); *A61P 31/04* (2018.01); *A61P 31/12* (2018.01); *A61P 33/02* (2018.01); *A61P 35/00* (2018.01); *A61P 37/06* (2018.01); *A61P 37/08* (2018.01); *A61K 48/00* (2013.01); *A61K 2039/53* (2013.01)

(58) Field of Classification Search
USPC ........................................................ 536/24.5
See application file for complete search history.

(56) References Cited

U.S. PATENT DOCUMENTS

| | | | |
|---|---|---|---|
| 2002/0150626 A1* | 10/2002 | Kohane | A61K 9/1617 424/493 |
| 2005/0032730 A1 | 2/2005 | Von der Mulbe et al. | |
| 2005/0059624 A1 | 3/2005 | Hoerr et al. | |
| 2005/0250723 A1 | 11/2005 | Hoerr et al. | |
| 2006/0188490 A1 | 8/2006 | Hoerr et al. | |
| 2007/0172430 A1 | 7/2007 | Brito et al. | |
| 2008/0025944 A1 | 1/2008 | Hoerr et al. | |
| 2008/0267873 A1 | 10/2008 | Hoerr et al. | |
| 2009/0324584 A1 | 12/2009 | Hoerr et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2010/0291156 A1 | 11/2010 | Barner et al. | |
| 2010/0305196 A1 | 12/2010 | Probst et al. | |

(Continued)

FOREIGN PATENT DOCUMENTS

| | | |
|---|---|---|
| WO | WO 2016/165825 | 10/1916 |
| WO | WO 2016/165831 | 10/1916 |

(Continued)

OTHER PUBLICATIONS

Mini-Buchi Spray Dryer (Technical specification sheet downloaded Buchi.com on May 20, 2019).*

(Continued)

*Primary Examiner* — Kimberly Chong
(74) *Attorney, Agent, or Firm* — Parker Highlander PLLC

(57) ABSTRACT

The present invention is directed to a storage-stable formulation of long-chain RNA. In particular, the invention concerns a dry powder composition comprising a long-chain RNA molecule. The present invention is furthermore directed to methods for preparing a dry powder composition comprising a long-chain RNA molecule by spray-drying. The invention further concerns the use of such a dry powder composition comprising a long-chain RNA molecule in the preparation of pharmaceutical compositions and vaccines, to a method of treating or preventing a disorder or a disease, to first and second medical uses of such a dry powder composition comprising a long-chain RNA molecule and to kits, particularly to kits of parts, comprising such a dry powder composition comprising a long-chain RNA molecule.

15 Claims, 12 Drawing Sheets
Specification includes a Sequence Listing.

(56) References Cited

U.S. PATENT DOCUMENTS

| | | |
|---|---|---|
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2015/0037326 A1 | 2/2015 | Butler-Ransohoff et al. |
| 2015/0050302 A1 | 2/2015 | Thess |
| 2015/0057340 A1 | 2/2015 | Thess et al. |
| 2015/0093413 A1 | 4/2015 | Thess et al. |
| 2015/0118183 A1 | 4/2015 | Baumhof |
| 2015/0118264 A1 | 4/2015 | Baumhof et al. |
| 2015/0165006 A1 | 6/2015 | Thess et al. |
| 2015/0184195 A1 | 7/2015 | Thess |
| 2015/0218554 A1 | 8/2015 | Thess |
| 2015/0306249 A1 | 10/2015 | Baumhof et al. |
| 2015/0320847 A1 | 11/2015 | Thess et al. |
| 2016/0130345 A1 | 5/2016 | Fotin-Mleczek et al. |
| 2016/0166668 A1 | 6/2016 | Kallen et al. |
| 2016/0166678 A1 | 6/2016 | Kallen et al. |
| 2016/0166710 A1 | 6/2016 | Baumhof |
| 2016/0166711 A1 | 6/2016 | Schnee et al. |
| 2016/0168207 A1 | 6/2016 | Kramps et al. |
| 2016/0168227 A1 | 6/2016 | Kallen et al. |
| 2016/0235864 A1 | 8/2016 | Schlake |
| 2016/0304883 A1 | 10/2016 | Grund |
| 2016/0304938 A1 | 10/2016 | Wochner |
| 2016/0326575 A1 | 11/2016 | Von Der Mulbe |
| 2016/0331844 A1 | 11/2016 | Fotin-Mleczek et al. |
| 2017/0014496 A1 | 1/2017 | Fotin-Mleczek et al. |
| 2017/0029847 A1 | 2/2017 | Thess |
| 2017/0114378 A1 | 4/2017 | Wocner et al. |
| 2017/0252430 A1 | 9/2017 | Fotin-Mleczek |
| 2017/0304459 A1 * | 10/2017 | Jadhav ................ A61K 9/0075 |
| 2017/0326225 A1 | 11/2017 | Rauch |
| 2018/0044687 A1 | 2/2018 | Thess et al. |
| 2018/0125952 A1 | 5/2018 | Fotin-Mleczek |
| 2018/0126003 A1 | 5/2018 | Hoerr |
| 2018/0142275 A1 | 5/2018 | Roos et al. |
| 2018/0147146 A1 | 5/2018 | Eber et al. |
| 2018/0148727 A1 | 5/2018 | Grund |

FOREIGN PATENT DOCUMENTS

| | | |
|---|---|---|
| WO | WO 2016/174227 | 11/1916 |
| WO | WO 2016/184576 | 11/1916 |
| WO | WO 2016/193206 | 12/1916 |
| WO | WO 2016/193226 | 12/1916 |
| WO | WO 2016/203025 | 12/1916 |
| WO | WO 2017/001058 | 1/1917 |
| WO | WO 2017/009376 | 1/1917 |
| WO | WO 2017/021546 | 2/1917 |
| WO | WO 2017/025120 | 2/1917 |
| WO | WO 2017/025447 | 2/1917 |
| WO | WO 2017/036580 | 3/1917 |
| WO | WO 2017/064146 | 4/1917 |
| WO | WO 2017/081110 | 5/1917 |
| WO | WO 2017/108087 | 6/1917 |
| WO | WO 2017/109134 | 6/1917 |
| WO | WO 2017/109161 | 6/1917 |
| WO | WO 2011/069528 | 6/2011 |
| WO | WO 2011/069529 | 6/2011 |

OTHER PUBLICATIONS

International Preliminary Report Patentability issued in corresponding PCT Application No. PCT/EP2016/000843, dated Nov. 15, 2016.

International Search Report and Written Opinion issued in corresponding PCT Application No. PCT/EP2016/000843, dated Nov. 15, 2016.

Jensen et al., "Spray drying of siRNA-containing PLGA nanoparticles intended for inhalation," *J. Control. Release*, 142(1):138-145, 2010.

* cited by examiner

R2564 (SEQ ID NO: 1)
GGGGCGCUGCCUACGGAGGUGGCAGCCAUCUCCUUCUCGGCAUCAAGCUUACCAUGAAGG
CCAUCCUGGUGGUCCUCCUGUACACCUUCGCCACCGCGAACGCCGACACGCUGUGCAUCG
GCUACCACGCCAACAACAGCACCGACACCGUGGACACCGUGCUCGAGAAGAACGUCACGG
UGACCCACUCCGUGAACCUGCUGGAGGACAAGCACAACGGGAAGCUCUGCAAGCUGCGGG
GCGUCGCCCCGCUGCACCUCGGGAAGUGCAACAUCGCCGGCUGGAUCCUGGGGAACCCGG
AGUGCGAGAGCCUGUCCACCGCGAGCUCCUGGAGCUACAUCGUGGAGACCUCCAGCUCCG
ACAACGGCACGUGCUACCCCGGCGACUUCAUCGACUACGAGGAGCUCCGCGAGCAGCUGA
GCUCCGUGAGCUCCUUCGAGCGGUUCGAGAUCUUCCCCAAGACCAGCUCCUGGCCCAACC
ACGACAGCAACAAGGGGGUCACCGCCGCCUGCCCGCACGCCGGCGCGAAGUCCUUCUACA
AGAACCUGAUCUGGCUCGUGAAGAAGGGGAACAGCUACCCCAAGCUGUCCAAGAGCUACA
UCAACGACAAGGGCAAGGAGGUGCUGGUCCUCUGGGGGAUCCACCACCCCAGCACCUCCG
CCGACCAGCAGAGCCUGUACCAGAACGCCGACGCCUACGUGUUCGUGGGCUCCAGCCGCU
ACUCCAAGAAGUUCAAGCCCGAGAUCGCCAUCCGGCCGAAGGUCCGCGACCAGGAGGGCC
GGAUGAACUACUACUGGACGCUGGUGGAGCCCGGGGACAAGAUCACCUUCGAGGCGACCG
GCAACCUCGUGGUCCCCGCUACGCCUUCGCCAUGGAGCGGAACGCCGGGAGCGGCAUCA
UCAUCUCCGACACCCCCGUGCACGACUGCAACACGACCUGCCAGACCCCGAAGGGCGCCA
UCAACACCAGCCUGCCCUUCCAGAACAUCCACCCCAUCACGAUCGGGAAGUGCCCCAAGU
ACGUGAAGUCCACCAAGCUGCGCCUCGCGACCGGCCUGCGGAACGUCCCGAGCAUCCAGU
CCCGCGGGCUGUUCGGCGCCAUCGCCGGGUUCAUCGAGGGCGGCUGGACCGGGAUGGUGG
ACGGCUGGUACGGGUACCACCACCAGAACGAGCAGGGCAGCGGGUACGCCGCCGACCUCA
AGUCCACGCAGAACGCGAUCGACGAGAUCACCAACAAGGUGAACAGCGUCAUCGAGAAGA
UGAACACCCAGUUCACCGCCGUGGGCAAGGAGUUCAACCACCUGGAGAAGCGGAUCGAGA
ACCUGAACAAGAAGGUCGACGACGGCUUCCUCGACAUCUGGACGUACAACGCCGAGCUGC
UGGUGCUCCUGGAGAACGAGCGCACCCUGGACUACCACGACUCCAACGUGAAGAACCUCU
ACGAGAAGGUCCGGAGCCAGCUGAAGAACAACGCCAAGGAGAUCGGGAACGGCUGCUUCG
AGUUCUACCACAAGUGCGACAACACCUGCAUGGAGUCCGUGAAGAACGGGACCUACGACU
ACCCCAAGUACAGCGAGGAGGCCAAGCUGAACCGCGAGGAGAUCGACGGCGUGAAGCUCG
AGUCCACGCGGAUCUACCAGAUCCUGGCGAUCUACAGCACCGUCGCCAGCUCCCUGGUGC
UCGUGGUCAGCCUGGGGGCCAUCUCCUUCUGGAUGUGCAGCAACGGCUCCCUGCAGUGCC
GCAUCUGCAUCUGACCACUAGUGCAUCACAUUUAAAAGCAUCUCAGCCUACCAUGAGAAU
AAGAGAAAGAAAAUGAAGAUCAAUAGCUUAUUCAUCUCUUUUUCUUUUUCGUUGGUGUAA
AGCCAACACCCUGUCUAAAAAACAUAAAUUUCUUUAAUCAUUUUGCCUCUUUUCUCUGUG
CUUCAAUUAAUAAAAAUGGAAAGAACCUAGAUCUAAAAAAAAAAAAAAAAAAAAAAAAAA
AAAAAAAAAAAAAAAAAAAAAAAAAAAAAAAAAAAAAAAAUGCAUCCCCCCCCCCCCCCC
CCCCCCCCCCCCCCAAAGGCUCUUUUCAGAGCCACCAGAAUU

DRY POWDER COMPOSITION COMPRISING LONG-CHAIN RNA

The present invention was made with support from the Government under Agreement No. HR0011-11-3-0001 awarded by DARPA. The Government has certain rights in the invention.

This application is a national phase application under 35 U.S.C. § 371 of International Application No. PCT/EP2016/000842, filed May 20, 2016, which claims benefit of European Application No. 15001517.0, filed May 20, 2015, and International Application No. PCT/EP2015/002019, filed Oct. 13, 2015, the entire contents of each of which are hereby incorporated by reference.

The present invention is directed to a storage-stable formulation of long-chain RNA. In particular, the invention concerns a dry powder composition comprising a long-chain RNA molecule. The present invention is furthermore directed to methods for preparing a dry powder composition comprising a long-chain RNA molecule by spray-drying. The invention further concerns the use of such a dry powder composition comprising a long-chain RNA molecule in the preparation of pharmaceutical compositions and vaccines, to a method of treating or preventing a disorder or a disease, to first and second medical uses of such a dry powder composition comprising a long-chain RNA molecule and to kits, particularly to kits of parts, comprising such a dry powder composition comprising a long-chain RNA molecule.

In gene therapy and many other therapeutically relevant biochemical and biotechnological applications, the use of nucleic acid molecules for therapeutic and diagnostic purposes is of major importance. For example, rapid progress has occurred in recent years in the field of gene therapy, where promising results have been achieved. Nucleic acids are therefore regarded as important tools for gene therapy and prophylactic and therapeutic vaccination against infectious and malignant diseases.

Other than DNA, application of RNA also represents a favored tool in modern molecular medicine. It also exhibits some superior properties over DNA cell transfection. As generally known, transfection of DNA molecules may lead to serious complications. For example, application of DNA molecules bears the risk that the DNA integrates into the host genome. Integration of foreign DNA into the host genome can have an influence on the expression of host genes and can trigger the expression of an oncogene or the inactivation of a tumor suppressor gene. Furthermore, an essential gene—and, as a consequence, the product of such an essential gene—may also be inactivated by the integration of the foreign DNA into the coding region of the gene. The result of such an event may be particularly dangerous if the DNA is integrated into a gene, which is involved in regulation of cell growth. Notwithstanding the risks associated with its application, DNA still represents an important tool. However, these risks do not occur if RNA, particularly mRNA, is used instead of DNA. An advantage of using RNA rather than DNA is that no virus-derived promoter element has to be administered in vivo and no integration into the genome may occur. Furthermore, the RNA, in order to exert its function, does not need to overcome the barrier to the nucleus.

However, a main disadvantage of the use of RNA is its instability. Even though it is understood that DNA, such as naked DNA, when introduced into a patient circulatory system, is typically not stable and therefore may have little chance of affecting most disease processes (see e.g. Poxon et al., Pharmaceutical development and Technology, 5(1), 115-122 (2000)), the problem of stability becomes even more prominent in the case of RNA. It is generally known that the physico-chemical stability of RNA molecules in solution is extremely low. RNA is susceptible to hydrolysis by ubiquitous ribonucleases or by divalent cations and is typically rapidly degraded, e.g. already after a few hours or days in solution. Rapid degradation occurs even in the absence of RNases, e.g. when RNA is stored in solution at room temperature for a few hours or days.

To avoid such rapid degradation, RNA (in solution) is typically stored at $-20°$ C. or even $-80°$ C. and under RNAse free conditions to prevent degradation of the RNA. Such storage conditions, however, do not sufficiently prevent a loss of function over time. Additionally, applying such conditions is very cost-intensive, especially for shipping and storage, e.g. whenever such low temperatures have to be guaranteed.

The only method for stabilization of long-chain RNA, which is known and applied, comprises lyophilization or freeze-drying of the RNA (see e.g. WO2011/069587 and WO2011/069586). Lyophilization is a method, which is known and recognized in the art to enhance storage stability of temperature sensitive biomolecules, such as nucleic acids. During lyophilization, water is typically removed from a frozen sample containing nucleic acids via sublimation. The process of lyophilization is usually characterized by a primary and a secondary drying step. In the primary drying step, free, i.e. unbound, water surrounding the nucleic acid (sequence) and optionally further components, evaporates from the frozen solution. Subsequently, water that is bound by the nucleic acids on a molecular basis may be removed in a secondary drying step by adding thermal energy. Thereby, the hydration sphere surrounding the nucleic acids is lost. Lyophilization is the most common processing method for removing moisture from biopharmaceuticals, and it can increase stability, temperature tolerance, and shelf life of these products. However, lyphilization does have its limitations, especially if scale-up is needed. One major disadvantage of lyophilization is that every single vial containing a sample has to be lyophilized separately. The lyophilized product cannot be separated into distinct charges or aliquots, as the lyophilized product is not provided e.g. in powder form. Instead, a cake-like product is obtained by lyophilization, which cannot be divided into distinct charges or aliquots. Therefore, if a powder-like product is desired, a further step of granulation must be carried out. At present, lyophilization of samples for a scaled-up production involves cost-intensive equipment, since, for example, a lot of lyophilizers are needed for market production, requiring large production facilities. Together with the time required for lyophilization and the additional requirement of a granulation step that renders lyophilization a technique, which is often not suitable for industrial scale production. Especially in an environment where budgets are tightening, and where time and facility space are at a premium, lyophilization may not be considered, e.g. by the pharmaceutical industry, as a competitive process.

A minor number of case reports refer to spray-dried ribonucleotides. Double-stranded short interfering RNAs (siRNA) for inhalation were dried by using a spray-drying technology. Jensen et al. (2010) studied parameters to be applied in spray drying of siRNA-loaded poly(D,L-lactide-co-glycolide) (PLGA) nanoparticles (NPs) for providing nano-composite micro-particles for inhalation. As siRNA was believed to denature at temperatures above 55° C., that study applied relatively low drying temperatures ($T_{inlet}$=45°

C.; $T_{outlet}$=30° C.) and high excipient concentrations (10-30%) to achieve a dry powder with a residual humidity of less than 4%.

US2011/077284 discloses the provision of dry powders of therapeutic and inhalable short siRNAs against influenza virus. Therein, drying temperatures were determined experimentally. Generally, the inlet temperature was from about 65° C. to about 125° C., while the outlet temperature ranged from about 30° C. to about 70° C. In the examples presented therein, siRNAs are dried at a $T_{outlet}$ of ≤55° C. The powders generally had a moisture content of typically less than 10% by weight, or less than 5% by weight, or less than 3% by weight. Also, the study characterized the chemical stability of the dry powder. Less than 10% by weight of the active siRNA were degraded upon storage of the dry powder composition under ambient conditions for a period of 18 months. However, the biological activity of the siRNA stored as a dry powder was not determined.

Summarizing the above, there is a long-lasting and urgent need in the art to provide means, which allow (a skilled person) to store long-chain RNA without loss of activity, an effect, which is commonly observed, particularly in in vivo applications. In this context, a challenging problem resulting from prior art approaches is to ensure stability of nucleic acids, particularly stability upon storage and delivery of longer single-stranded RNA. Another problem of the prior art is the loss of biological activity of nucleic acids subsequent to storage. Finally, by using prior art methods, only small amounts of nucleic acid are obtained. The provision of a suitable form for delivering these nucleic acids but also the production, transport and storage thereof, especially transport of RNA, is an issue due to the conditions to ensure temperatures of −20° C. and less for shipment. Furthermore, lyophilization of long-chain RNA, especially for the use as medicament, bears the problem that it is very cost- and time-intensive, particularly if commercial production in a scaled-up process is envisaged.

The underlying object is therefore to provide a nucleic acid molecule, in particular a long-chain RNA, exhibiting no loss of activity when stored prior to its use and being available by cost-avoiding production process. In particular, it is an object of the present invention to provide a long-chain RNA molecule in a storage-stable formulation. One object of the invention is to provide a dry powder composition comprising a long-chain RNA molecule. In addition, it is an objective of the invention to provide a method for preparing a dry powder comprising a long-chain RNA molecule, wherein the RNA molecule retains its chemical integrity and its biological activity. It is another object of the present invention that such methods are applicable under industrial large-scale production conditions, preferably by a continuous process. It is a particular object to provide a method that allows drying a liquid comprising long-chain RNA molecules.

The object underlying the present invention is solved by the claimed subject-matter.

In a first aspect, the invention relates to a long-chain RNA molecule in a particulate formulation. In particular, the invention concerns a dry powder composition comprising a long-chain RNA molecule. Prior to the invention described herein, long-chain RNA (in contrast to shorter double-stranded RNAs) was never provided as a dry powder composition. Advantageously, the dry powder composition according to the invention provides a storage-stable form of a long-chain RNA molecule. In addition, the dry powder composition according to the invention is characterized by superior handling properties. For example, the inventive dry powder composition can be packaged in any quantity or in any container or dosage form, respectively. Handling of the dry powder composition according to the invention is further improved by its free-flowing properties. In particular, the inventive dry powder composition does not form agglomerates or aggregates that would inhibit packaging and/or dosage. Due to its flowability, the dry powder composition according to the invention can be readily further processed. For instance, the dry powder composition can be transferred, e.g. from one vessel to another or from a larger vessel into a plurality of smaller vessels, simply by pouring. The inventive dry powder composition can readily be packaged in a variety of packages and final dosage forms according to the actual requirements. Advantageously, the dry powder composition according to the invention provides excellent storage stability.

In particular, the invention provides a dry powder composition comprising a long-chain RNA molecule, wherein the long-chain RNA molecule preferably comprises at least 30 nucleotides. Preferably, the long-chain RNA molecule is a molecule as defined herein. More preferably, the long-chain RNA molecule is not an RNA molecule selected from the group consisting of a small interfering RNA (siRNA), a microRNA, a small nuclear RNA (snRNA), a small-hairpin (sh) RNA, a riboswitch, a ribozyme or an aptamer. Even more preferably, the long-chain RNA is not an siRNA, most preferably not a double-stranded siRNA.

In a preferred embodiment, the dry powder composition as described herein does not comprise an RNA molecule comprising less than 30 nucleotides, less than 200 nucleotides or less than 250 nucleotides. The dry powder composition does preferably not comprise an RNA molecule selected from the group consisting of a small interfering RNA (siRNA), preferably a single-stranded or a double-stranded siRNA, a microRNA, a small nuclear RNA (snRNA), a small-hairpin (sh) RNA, a riboswitch, a ribozyme or an aptamer. Even more preferably, the dry powder composition does not comprise an siRNA, most preferably not a double-stranded siRNA.

With respect to the following description of the inventive dry powder composition it is noted that the definitions and specifications provided therein may also be applied to the inventive method, which is subsequently described as another aspect of the invention.

In the context of the present invention, the term "dry powder" (or "dry powder composition") typically refers to a composition that is—amongst other features—characterized by its residual moisture content, which is preferably low enough in order to prevent the formation of aggregates that would reduce or inhibit the flowability of the powder. As used herein, the term "residual moisture content" (or "residual moisture") typically refers to the total amount of solvent present in the dry powder composition. Said total amount of residual solvents in the dry powder composition is determined using any suitable method known in the art. For example, methods for determining the residual moisture content comprise the Karl-Fischer-titrimetric technique or the thermal gravimetric analysis (TGA) method. In a preferred embodiment, the residual solvent comprised in the dry powder composition is water or an essentially aqueous solution and the residual moisture content corresponds to the residual water content of the dry powder composition, which is determined by the Karl-Fischer-titrimetric technique. Without being bound by any theory, the low residual moisture content of the inventive dry powder composition is expected to contribute to its excellent storage stability.

Preferably, the residual moisture content of the dry powder composition according to the invention is 15% (w/w) or less, more preferably 10% (w/w) or less, even more preferably 9% (w/w), 8% (w/w), 7% (w/w), 6% (w/w) or 5% (w/w). In a preferred embodiment, the residual moisture content of the dry powder composition is 5% (w/w) or less, preferably 4% (w/w) or less. In a particularly preferred embodiment, the residual moisture content is 7% (w/w) or less. In a further preferred embodiment, the residual moisture content of the dry powder composition in the range from 0% to 15% (w/w), from 0% to 10% (w/w), from 0% to 7% (w/w), from 0% to 5% (w/w), from 0% to 4% (w/w), from 3% to 6% (w/w) or from 2% to 5% (w/w).

In a further preferred embodiment, the residual moisture content of the dry powder composition as described herein is 5% (w/w) or less, more preferably 4% (w/w) or less, even more preferably 3% (w/w) or less, 2% (w/w) or less, or 1% (w/w) or less. Alternatively, the residual moisture content of the dry powder composition as described herein is preferably in the range from 0% to 5% (w/w), from 0% to 4% (w/w), from 0% to 3% (w/w), from 0% to 2% (w/w) or from 0% to 1% (w/w).

In a further preferred embodiment, the present invention provides a dry powder composition having a residual water content of 15% (w/w) or less, more preferably 10% (w/w) or less, even more preferably 9% (w/w), 8% (w/w), 7% (w/w), 6% (w/w) or 5% (w/w). According to a preferred embodiment, the residual water content of the dry powder composition is 5% (w/w) or less, preferably 4% (w/w) or less. In a particularly preferred embodiment, the residual water is 7% (w/w) or less. In a further preferred embodiment, the residual water content of the dry powder composition in the range from 0% to 15% (w/w), from 0% to 10% (w/w), from 0% to 7% (w/w), from 0% to 5% (w/w), from 0% to 4% (w/w), from 3% to 6% (w/w) or from 2% to 5% (w/w).

Preferably, the dry powder composition comprising a long-chain RNA molecule comprises a plurality of particles. Therein, the term "particle" typically refers to an individual solid particle of the dry powder composition. The individual particles of the dry powder composition according to the invention are preferably physically separated from each other, i.e. the individual particles that constitute the dry powder may be in lose and reversible contact with each other (as opposed to an irreversible link between individual particles). Preferably, the term "particle" refers to the smallest physical entity of the inventive dry powder composition. The particles of the inventive dry powder composition do preferably not stick to each other. The particulate nature of the formulation contributes to the superior characteristics of the inventive dry powder composition, e.g. its free flowability.

In a preferred embodiment, the plurality of individual particles of the dry powder composition according to the invention is characterized by a size distribution, wherein the size of individual particles may be the same or different from each other. Typically, the size of the particles of a dry powder composition is characterized by a Gaussian distribution or a quasi-Gaussian distribution. Preferably, the dry powder composition according to the invention is characterized by a volume weighted particle size distribution as determined, for instance, by static light scattering techniques, such as laser diffraction, or by using a cascade impactor. In a volume weighted distribution, the contribution of each particle in the dry powder composition relates to the volume of that particle. The dry powder composition according to the invention is preferably characterized by parameters such as, for example, Dv10, Dv50, Dv90 or the mass median aerodynamic diameter (MMAD).

The parameter "Dv50" (or "volume D50" or "volume weighted D50") relates to the median particle size based on a volume weighted particle size distribution. Dv50 thus typically describes the particle size (based on a volume weighted distribution), preferably the diameter of a particle in micrometers (μm), with 50% of the particles in the distribution having a larger size and 50% of the particles in the distribution having a smaller size than Dv50. In a volume weighted distribution, the parameter "Dv50" typically relates to the diameter (e.g. in micrometers) of a hypothetical spherical particle, which has the volume of the corresponding actual particle in the distribution (which may or may not be spherical).

Analogously, the parameter "Dv10" corresponds to the cut-off size (preferably in μm) of the particles in a volume weighted distribution, which represent 10% of the total volume of the sample, and which have a particle size equal to or smaller than the Dv10 value. Preferably, the Dv10 of the dry powder composition according to the invention is at least 0.2, 0.3, 0.4, 0.5, 1, 2, 3, 4, 5, 6, 7, 8, 9, or 10 μm. More preferably, the Dv10 of the dry powder composition is equal to or lower than 5, equal to or lower than 10, or equal to or lower than 20 μm. Most preferably, the Dv10 is in a range from 1 μm to 10 μm or from about 3 μm to about 5 μm.

The parameter "Dv90" corresponds to the cut-off size (preferably in μm) of the particles in a volume weighted distribution, which represent 90% of the total volume of the sample, and which have a particle size equal to or smaller than the Dv90 value. Preferably, the Dv90 of the dry powder composition according to the invention is at least 1, 2, 3, 4, 5, 6, 7, 8, 9, 10, 15, 20, 25, 30, 35, 40, 45 or 50 μm. Preferably, the Dv90 of the dry powder composition according to the invention is equal to or lower than 1.500, 1.250, 1.000, 750, 600, 500, 400, 300, 200 or 100 μm. More preferably, the Dv90 may be in a range from 0.3 μm to 2.000 μm, from 1 μm to 1.000 μm, from 2 μm to 500 μm or from 2 μm to 200 μm. In a preferred embodiment, the Dv90 of the dry powder composition is at least 1 μm or in the range from 1 to 200 μm. In a particularly preferred embodiment, the Dv90 of the dry powder composition is at least 3 μm, at least 5 μm or at least 20 μm.

The mass median aerodynamic diameter (MMAD) describes the particle size based on the aerodynamic properties of the respective particle, in particular its settling behaviour. The MMAD is preferably determined using any suitable instrument known in the art, such as, for instance, an APS™ spectrometer (TSI Inc.). The MMAD relates to the median aerodynamic diameter of the particle distribution and is the diameter of a unit density sphere having the same settling velocity, in air, as the particle. The MMAD thus typically describes the particle size, preferably in micrometers (μm), with 50% of the particles in the distribution having a larger size and 50% of the particles in the distribution having a smaller size than the MMAD value. Preferably, the dry powder composition according to the invention is characterized by a MMAD of at least 0.3 μm. Alternatively, the MMAD of the dry powder composition according to the invention is at least 1, 2, 3, 4, 5, 6, 7, 8, 9, 10, 15, 20, 25, 30, 35, 40, 45 or 50 μm. Preferably, the MMAD of the dry powder composition according to the invention is equal to or less than 1.500, 1.250, 1.000, 750, 600, 500, 400, 300, 200 or 100 μm. Further preferably, MMAD may be in a range from 0.3 μm to 2.000 μm, from 1 μm to 1.000 μm, from 2 μm to 500 μm or from 2 μm to 200 μm. In a preferred embodiment, the MMAD of the dry powder composition is at least 1 µm or in the range from 1 to 200 µm. In a particularly preferred embodiment, the MMAD of the dry powder composition is at least 3 µm, at least 5 µm or at least 20 µm.

The dry powder composition is preferably characterized by using the span of the particle size distribution as a parameter. Therein, the span (for a volume weighted distribution) is defined according to the following formula $$\mathrm{Span} = \frac{Dv90 - Dv10}{Dv50}$$

For distributions, which are not volume weighted, the Dv values in the formula above are respectively replaced by the corresponding Dx values, e.g. Dn90 for a number weighted distribution. In a preferred embodiment, the inventive dry powder composition is characterized by a low span value, which indicates a narrow (or more homogeneous) particle size distribution. Typically, a narrow distribution enhances the flowability of the dry powder composition. Preferably, the span of the dry powder composition according to the present invention is equal to or less than 5, more preferably equal to or less than 4, and even more preferably equal to or less than 3. In a particularly preferred embodiment, the particle size distribution of the dry powder composition according to the invention is characterized by a span of equal to or less than about 2 or a span of equal to or less than about 1.5.

In a preferred embodiment, the dry powder composition comprises a plurality of spherical particles. As used herein, the term "spherical" comprises not only geometrically perfect spheres, but also more irregular shapes, such as spheroidal, elipsoid, oval or rounded particles. The shape of an individual particle can be determined by known methods and by using instruments, which are commercially available, such as Lasentec™ (particle chord length FBRM), Malvern™ (Fraunhofer diffraction) or Coulter Counter™ (electric zone sensing). Typically, the volume and the surface area of an individual particle are determined. By using such parameters, Waddell's sphericity ψ (herein also referred to as "sphericity" or "circularity") may be calculated, e.g. by using the following formula $$\psi = \frac{\text{surface area of sphere of equal volume to the particle}}{\text{surface area of the particle}}$$

It is preferred that the average sphericity of the particles, which are contained in the inventive dry powder composition, is at least 0.7, preferably at least 0.75, at least 0.8, at least 0.85, at least 0.9, at least 0.95 or 1. Preferably, the average sphericity of the particles, which are contained in the dry powder composition, is in the range from 0.7 to 1, more preferably in the range from 0.8 to 1, from 0.85 to 1, or from 0.9 to 1. In a particularly preferred embodiment, the average sphericity of the particles, which are contained in the inventive dry powder composition, is in the range from 0.7 to 1.

In another preferred embodiment, the dry powder composition according to the invention consists of particles, which are characterized by a sphericity of at least 0.7, preferably at least 0.75, at least 0.8, at least 0.85, at least 0.9, at least 0.95 or 1. Preferably, the dry powder composition consists of particles with a sphericity in the range from 0.7 to 1, more preferably in the range from 0.8 to 1, from 0.85 to 1, or from 0.9 to 1.

Alternatively, the sphericity of those particles of the dry powder composition that have a particle size equal to Dv50 as defined herein is at least 0.7, preferably at least 0.75, at least 0.8, at least 0.85, at least 0.9, at least 0.95 or 1. Preferably, the sphericity of those particles of the dry powder composition that have a particle size equal to Dv50 as defined herein is in the range from 0.7 to 1, more preferably in the range from 0.8 to 1, from 0.85 to 1, or from 0.9 to 1. Even more preferably, those particles of the dry powder composition that have a particle size equal to Dv90 as defined herein have a sphericity of at least 0.7, preferably of at least 0.75, at least 0.8, at least 0.85, at least 0.9, at least 0.95 or 1. Preferably, the sphericity of those particles of the dry powder composition that have a particle size equal to Dv90 as defined herein is in the range from 0.7 to 1, more preferably in the range from 0.8 to 1, from 0.85 to 1, or from 0.9 to 1.

Further preferably, the average sphericity of those particles of the dry powder composition that have a particle size equal to or lower than Dv50 as defined herein is at least 0.7, preferably at least 0.75, at least 0.8, at least 0.85, at least 0.9, at least 0.95 or 1. Preferably, the average sphericity of those particles of the dry powder composition that have a particle size equal to or lower than Dv50 as defined herein is in the range from 0.7 to 1, more preferably in the range from 0.8 to 1, from 0.85 to 1, or from 0.9 to 1. Even more preferably, the average sphericity of those particles of the dry powder composition that have a particle size equal to or lower than Dv90 as defined herein is at least 0.7, preferably of at least 0.75, at least 0.8, at least 0.85, at least 0.9, at least 0.95 or 1. Preferably, the average sphericity of those particles of the dry powder composition that have a particle size equal to or lower than Dv90 as defined herein is in the range from 0.7 to 1, more preferably in the range from 0.8 to 1, from 0.85 to 1, or from 0.9 to 1.

In the context of the present invention, the term "RNA" is used as abbreviation for ribonucleic acid. RNA is a nucleic acid molecule, i.e. a polymer consisting of nucleotides. These nucleotides are usually adenosine-monophosphate, uridine-monophosphate, guanosine-monophosphate and cytidine-monophosphate monomers, which are connected to each other along a so-called backbone. The backbone is formed by phosphodiester bonds between the sugar, i.e. ribose, of a first and a phosphate moiety of a second, adjacent monomer. The specific succession of the monomers is called the RNA sequence. As used herein, the term "RNA molecule" is not limited to any particular type of RNA.

For example, RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA, which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a (mature) mRNA comprises a 5'-cap, optionally a 5'UTR, an open reading frame, optionally a 3'UTR and a poly(A) and/or poly(C) sequence. Furthermore, the term "RNA molecule" comprises ribonucleic acids comprising more than one open reading frame, such as bicistronic or multicistronic RNA molecules. A bicistronic or multicistronic RNA molecule is typically an RNA molecule, preferably an mRNA molecule, that may typically have two (bicistronic) or more (multicistronic) open reading frames (ORF).

Aside from messenger RNA, several non-coding types of RNA exist, which may be involved in regulation of transcription and/or translation, such as a ribosomal RNA (rRNA) or a transfer RNA (tRNA). The terms "RNA" or "RNA molecule" further encompass other coding RNA molecules, such as viral RNA, retroviral RNA, self-replicating RNA (replicon RNA), small interfering RNA (siRNA), microRNA, small nuclear RNA (snRNA), small-hairpin (sh) RNA, riboswitches, ribozymes or an aptamers.

The term "long-chain RNA molecule" (or "long-chain RNA") as used herein typically refers to an RNA molecule, preferably as described herein, which preferably comprises at least 30 nucleotides. Alternatively, the long-chain RNA molecule according to the invention may comprise at least 35, 40, 45, 50, 55, 60, 65, 70, 75, 80, 85, 90, 95, 100, 150, 200, 250, 300, 350, 400, 450 or at least 500 nucleotides. In a preferred embodiment, the long-chain RNA molecule comprises at least 100 nucleotides, even more preferably at least 200 nucleotides. The long-chain RNA molecule further preferably comprises from 30 to 50.000 nucleotides, from 30 to 20.000 nucleotides, from 100 to 20.000 nucleotides, from 200 to 20.000 nucleotides, from 250 to 15.000 nucleotides or from 500 to 20.000 nucleotides.

According to a preferred embodiment, the long-chain RNA of the dry powder composition as described herein comprises more than 200 nucleotides, preferably at least 250 nucleotides. Alternatively, the long-chain RNA as described herein may comprise more than 210, more than 220, more than 230, more than 240, more than 250, more than 260, more than 270, more than 280, more than 290, more than 300, more than 350, more than 400, more than 450 or more than 500 nucleotides. More preferably, the long-chain RNA as described herein may comprise at least about 210, at least about 220, at least about 230, at least about 240, at least about 250, at least about 260, at least about 270, at least about 280, at least about 290, at least about 300, at least about 350, at least about 400, at least about 450 or at least about 500 nucleotides.

The inventive dry powder composition comprises a (first) long-chain RNA molecule and may further comprise a second or further RNA molecule, which may also be a long-chain RNA molecule, preferably as defined herein. Preferably, the second or further RNA molecule comprised in the dry powder composition is distinct from the (first) long-chain RNA molecule.

In a preferred embodiment, the long-chain RNA molecule comprised in the dry powder composition according to the invention is not an RNA molecule selected from the group consisting of a small interfering RNA (siRNA), a microRNA, a small nuclear RNA (snRNA), a small-hairpin (sh) RNA or riboswitch, a ribozyme, and an aptamer. More preferably, the long-chain RNA as described herein is not an siRNA, most preferably not a double-stranded siRNA.

As used herein, the term "RNA molecule" typically refers to a single-stranded or a double-stranded RNA molecule. In a preferred embodiment, the long-chain RNA molecule of the inventive dry powder composition is a single-stranded RNA molecule.

In a further embodiment, the long-chain RNA molecule comprised in the dry powder composition according to the invention is a coding RNA molecule or an immunostimulatory RNA molecule.

In a preferred embodiment, the long-chain RNA is a coding RNA, which comprises at least one open reading frame encoding a peptide or protein.

In the context of the present invention, the long-chain RNA molecule may be a coding RNA molecule encoding a protein or a peptide, which may be selected, without being restricted thereto, e.g. from therapeutically active proteins or peptides, selected e.g. from adjuvant proteins, from antigens, e.g. tumour antigens, pathogenic antigens (e.g. selected, from animal antigens, from viral antigens, from protozoan antigens, from bacterial antigens), allergenic antigens, autoimmune antigens, or further antigens, preferably as defined herein, from allergens, from antibodies, from immunostimulatory proteins or peptides, from antigen-specific T-cell receptors, or from any other protein or peptide suitable for a specific (therapeutic) application, wherein the coding RNA molecule may be transported into a cell, a tissue or an organism and the protein may be expressed subsequently in this cell, tissue or organism. In a particularly preferred embodiment, the long-chain RNA molecule is an mRNA molecule.

The long-chain RNA molecule of the dry powder composition may further be an immunostimulatory RNA molecule, such as any RNA molecule known in the art, which is capable of inducing an innate immune response. Particularly preferred in this context are immunostimulatory RNA molecules as described in WO 2009/095226.

The dry powder composition may further comprise a modified RNA molecule. In a preferred embodiment, the long-chain RNA molecule comprises at least one modification as described herein. Alternatively or additionally, the dry powder composition may comprise a second or further RNA molecule (distinct from the (first) long-chain RNA molecule), which comprises at least one modification as described herein. Preferably, the long-chain RNA molecule of the dry powder composition according to the invention comprises an RNA modification, which preferably increases the stability of the RNA molecule and/or the expression of a protein encoded by the RNA molecule. Several RNA modifications are known in the art, which can be applied to an RNA molecule in the context of the present invention.

Chemical Modifications:

The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications:

The modified nucleosides and nucleotides, which may be incorporated into a modified RNA molecule as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH$_2$; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications:

The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments, a modified RNA may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Lipid Modification:

According to a further embodiment, a modified RNA molecule as defined herein can contain a lipid modification. Such a lipid-modified RNA molecule typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an RNA molecule as defined herein, at least one linker covalently linked with that RNA molecule, and at least one lipid covalently linked with the respective linker, and also at least one (bifunctional) lipid covalently linked (without a linker) with that RNA molecule. In this context, it is particularly preferred that the lipid modification is present at the terminal ends of a linear RNA sequence.

Modification of the 5'-End of a Modified RNA Molecule:

According to another preferred embodiment of the invention, a modified RNA molecule as defined herein, can be modified by the addition of a so-called "5' CAP" structure.

A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in a modified RNA in this context. Accordingly, a modified RNA of the present invention may comprise a m7GpppN as 5'-CAP, but additionally the modified RNA comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification in this context.

Particularly preferred modified 5'-CAP structures are CAP1 (methylation of the ribose of the adjacent nucleotide of m7G), CAP2 (methylation of the ribose of the 2nd nucleotide downstream of the m7G), CAP3 (methylation of the ribose of the 3rd nucleotide downstream of the m7G), CAP4 (methylation of the ribose of the 4th nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In a preferred embodiment, the inventive dry powder composition comprises a modified RNA molecule having at least one open reading frame, which encodes at least one peptide or protein. Said modified RNA molecule having at least one open reading frame may be the (first) long-chain RNA molecule, preferably a long-chain mRNA molecule, or a second or further RNA molecule, which may be comprised in the dry powder composition in addition to the (first) long-chain RNA molecule. Preferably, the sequence of the open reading frame in such an RNA molecule is modified as described herein.

Modification of the G/C Content:

In a particularly preferred embodiment of the present invention, the G/C content of the coding region of a modified RNA comprised in the inventive dry powder composition, is modified, particularly increased, compared to the G/C content of its particular wild type coding region, i.e. the unmodified coding region. The encoded amino acid sequence of the coding region is preferably not modified compared to the coded amino acid sequence of the particular wild type coding region. The modification of the G/C-content of the coding region of the modified RNA as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage). Depending on the amino acid to be encoded by the coding region of the modified RNA as defined herein, there are various possibilities for modification of the RNA sequence, e.g. the coding region, compared to its wild type coding region. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present. In contrast, codons which contain A and/or U nucleotides can be modified by substitution of other codons which code for the same amino acids but contain no A and/or U. Examples of these are: the codons for Pro can be modified from CCU or CCA to CCC or CCG; the codons for Arg can be modified from CGU or CGA or AGA or AGG to CGC or CGG; the codons for Ala can be modified from GCU or GCA to GCC or GCG; the codons for Gly can be modified from GGU or GGA to GGC or GGG. In other cases, although A or U nucleotides cannot be eliminated from the codons, it is however possible to decrease the A and U content by using codons, which contain a lower content of A and/or U nucleotides. Examples of these are: the codons for Phe can be modified from UUU to UUC; the codons for Leu can be modified from UUA, UUG, CUU or CUA to CUC or CUG; the codons for Ser can be modified from UCU or UCA or AGU to UCC, UCG or AGC; the codon for Tyr can be modified from UAU to UAC; the codon for Cys can be modified from UGU to UGC; the codon for His can be modified from CAU to CAC; the codon for Gln can be modified from CAA to CAG; the codons for Ile can be modified from AUU or AUA to AUC; the codons for Thr can be modified from ACU or ACA to ACC or ACG; the codon for Asn can be modified from AAU to AAC; the codon for Lys can be modified from AAA to AAG; the codons for Val can be modified from GUU or GUA to GUC or GUG; the codon for Asp can be modified from GAU to GAC; the codon for Glu can be modified from GAA to GAG; the stop codon UAA can be modified to UAG or UGA. In the case of the codons for Met (AUG) and Trp (UGG), on the other hand, there is no possibility of sequence modification. The substitutions listed above can be used either individually or in any possible combination to increase the G/C content of the coding region of the modified RNA as defined herein, compared to its particular wild type coding region (i.e. the original sequence). Thus, for example, all codons for Thr occurring in the wild type sequence can be modified to ACC (or ACG).

Preferably, the G/C content of the coding region of the modified RNA as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein, which comprises a pathogenic antigen or a fragment, variant or derivative thereof, are substituted, thereby increasing the G/C content of said coding region. In this context, it is particularly preferable to increase the G/C content of the coding region of the modified RNA as defined herein, to the maximum (i.e. 100% of the substitutable codons), compared to the wild type coding region.

Codon Optimization:

According to the invention, a further preferred modification of the coding region encoding at least one peptide or protein of a modified RNA as defined herein, is based on the finding that the translation efficiency is also determined by a different frequency in the occurrence of tRNAs in cells. Thus, if so-called "rare codons" are present in the coding region of the wild type RNA sequence, to an increased extent, the mRNA is translated to a significantly poorer degree than in the case where codons coding for relatively "frequent" tRNAs are present. In this context, the coding region of the modified RNA is preferably modified compared to the corresponding wild type coding region such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the coding region of the modified RNA as defined herein, is modified such that codons, for which frequently occurring tRNAs are available, are inserted. In other words, according to the invention, by this modification all codons of the wild type coding region, which code for a tRNA which is relatively rare in the cell, can in each case be exchanged for a codon, which codes for a tRNA which is relatively frequent in the cell and which, in each case, carries the same amino acid as the relatively rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content, which is increased, in particular maximized, in the coding region of the modified RNA as defined herein, with the "frequent" codons without modifying the amino acid sequence of the peptide or protein encoded by the coding region of the RNA sequence. This preferred embodiment allows provision of a particularly efficiently translated and stabilized (modified) RNA sequence as defined herein.

In the context of the present invention, the long-chain RNA molecule may also comprise a 5'- and/or 3' untranslated region (5'-UTR or 3'-UTR, respectively). More preferably, the long-chain RNA molecule comprises a 5'-CAP structure.

Preferably, the long-chain RNA molecule further comprises a poly(A) sequence. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides. Most preferably, the long-chain RNA molecule comprises a poly(A) sequence of about 60 to about 70 nucleotides, most preferably 64 adenine nucleotides.

Preferably, the poly(A) sequence in the long-chain RNA molecule is derived from a DNA template by in vitro transcription. Alternatively, the poly(A) sequence may also be obtained in vitro by common methods of chemical-synthesis without being necessarily transcribed from a DNA-progenitor.

Alternatively, the long-chain RNA molecule optionally comprises a polyadenylation signal, which is defined herein as a signal, which conveys polyadenylation to a (transcribed) mRNA by specific protein factors (e.g. cleavage and polyadenylation specificity factor (CPSF), cleavage stimulation factor (CstF), cleavage factors I and II (CF I and CF II), poly(A) polymerase (PAP)). In this context, a consensus polyadenylation signal is preferred comprising the NN(U/T)ANA consensus sequence. In a particularly preferred aspect, the polyadenylation signal comprises one of the following sequences: AA(U/T)AAA or A(U/T)(U/T)AAA (wherein uridine is usually present in RNA and thymidine is usually present in DNA).

In addition or as an alternative to a poly(A) sequence as described above, the long-chain RNA molecule may also comprise a poly(C) sequence, preferably in the region 3' of the coding region of the RNA. A poly(C) sequence is typically a stretch of multiple cytosine nucleotides, typically about 10 to about 200 cytidine nucleotides, preferably about 10 to about 100 cytidine nucleotides, more preferably about 10 to about 70 cytidine nucleotides or even more preferably about 20 to about 50 or even about 20 to about 30 cytidine nucleotides. A poly(C) sequence may preferably be located 3' of the coding region comprised by a nucleic acid. In a preferred embodiment of the present invention, the long-chain RNA molecule comprises a poly(A) sequence and a poly(C) sequence, wherein the poly(C) sequence is located 3' of the poly(A) sequence.

In a particularly preferred embodiment, the long-chain RNA molecule in the context of the present invention comprises in 5'-to-3'-direction, a 5'-UTR, an open reading frame, preferably a modified open reading frame as defined herein, a 3'-UTR element and a poly(A) or a poly(C) sequence.

According to a preferred embodiment, the inventive dry powder composition may comprise the long-chain RNA molecule as described herein in free form ("naked RNA") or in the form of a complex with another compound, such as a transfection or complexation agent. For example, the long-chain RNA molecule may be present in the dry powder composition in a complex with a cationic or polycationic carrier or compound, which may serve as transfection or complexation agent. In a preferred embodiment, the dry powder composition comprises both, the long-chain RNA in free form as well in a complex with a cationic or polycationic carrier or compound. Such a complex of long-chain RNA with a cationic or polycationic carrier or compound may be present in the inventive dry powder composition or in an intermediate product as a nanoparticle, preferably as defined herein. The preparation of RNA complexes with polycationic or cationic compounds is known in the art and is preferably carried out as described in WO2010/037539 or WO2011/026641, the entire disclosure of which is herewith incorporated by reference.

In this context, the long-chain RNA molecule in the inventive dry powder composition is preferably complexed by a compound selected from the group of polymers or complexing agents, typically comprising, without being limited thereto, any polymer suitable for the preparation of a pharmaceutical composition, such as minor/major groove binders, nucleic acid binding proteins, lipoplexes, nanoplexes, non-cationic or non-polycationic compounds, such as PLGA, Polyacetate, Polyacrylate, PVA, Dextran, hydroxymethylcellulose, starch, MMP, PVP, heparin, pectin, hyaluronic acid, and derivatives thereof, or cationic or polycationic compound, particularly cationic or polycationic polymers or cationic or polycationic lipids, preferably a cationic or polycationic polymers. In the context of the present invention, such a cationic or polycationic compound is typically selected from any cationic or polycationic compound, suitable for complexing and thereby stabilizing a long-chain RNA molecule as defined herein, e.g. by associating the RNA molecule with the cationic or polycationic compound.

According to an alternative embodiment, the dry powder composition according to the invention comprises the long-chain RNA as described herein formulated together with one or more cationic or polycationic compounds, preferably with cationic or polycationic polymers, cationic or polycationic peptides or proteins, e.g. protamine, cationic or polycationic polysaccharides and/or cationic or polycationic lipids.

According to a preferred embodiment, the long-chain RNA as described herein may be complexed with lipids to form one or more liposomes, lipoplexes, or lipid nanoparticles. Therefore, in one embodiment, the dry powder composition comprises liposomes, lipoplexes, and/or lipid nanoparticles comprising the long-chain RNA.

Lipid-based formulations have been increasingly recognized as one of the most promising delivery systems for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and to deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behaviour in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications.

Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin RNA-shRNA). Cationic lipids, such as DOTAP, (1,2-dioleoyl-3-trimethylammonium-propane) and DOTMA (N-[1-(2,3-dioleoyloxy)propyl]-N,N,N-trimethyl-ammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv Rev. 2014 February; 66: 110-116.).

Therefore, in one embodiment the long-chain RNA of the dry powder composition as described herein is complexed with a cationic lipid and/or a neutral lipid and thereby forms liposomes, lipid nanoparticles, lipoplexes or neutral lipid-based nanoliposomes.

Particularly preferred complexation agents in this context are cationic or polycationic compounds, including protamine, nucleoline, spermine or spermidine, or other cationic peptides or proteins, such as poly-L-lysine (PLL), poly-arginine, oligoarginines as defined above, such as $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc., basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, plsl, FGF, Lactoferrin, Transportan, Buforin-2, Bac715-24, SynB, SynB(1), pVEC, hCT-derived peptides, SAP, or histones. In a particularly preferred embodiment, the dry powder composition according to the invention comprises protamin, wherein the long-chain RNA molecule is preferably complexed by protamine.

The dry powder composition according to the invention preferably comprises a cationic or polycationic compound in solution and/or in complex with the long-chain RNA molecule. More preferably, the inventive dry powder composition comprises a cationic or polycationic compound, preferably protamine, and the long-chain RNA molecule at a weight ratio (RNA:protamine, w/w) in a range from 1:10 to 10:1, more preferably from 5:1 to 1:1, even more preferably from 3:1 to 1:1. Most preferably, the weight ratio of the long-chain RNA molecule to cationic or polycationic compound, preferably protamine, in the composition is 2:1 (w/w).

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (I):

$$\{(Arg)_l;(Lys)_m;(His)_n;(Orn)_o;(Xaa)_x\}; \quad \text{formula (I)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context, cationic peptides or proteins in the range of 7-30 amino acids are particular preferred.

Further, the cationic or polycationic peptide or protein, when defined according to formula $\{(Arg)_l;(Lys)_m;(His)_n;(Orn)_o;(Xaa)_x\}$ (formula (I)) as shown above and which comprise or are additionally modified to comprise at least one —SH moiety, may be, without being restricted thereto, selected from subformula (Ia):

$$\{(Arg)_l;(Lys)_m;(His)_n;(Orn)_o;(Xaa')_x(Cys)_y\} \quad \text{subformula (Ia)}$$

wherein $(Arg)_l;(Lys)_m;(His)_n;(Orn)_o;$ and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (Ib):

$$Cys_1\{(Arg)_l;(Lys)_m;(His)_n;(Orn)_o;(Xaa)_x\}Cys_2 \quad \text{subformula (Ib)}$$

wherein empirical formula $\{(Arg)_l;(Lys)_m;(His)_n;(Orn)_o;(Xaa)_x\}$ (formula (I)) is as defined herein and forms a core of an amino acid sequence according to (semiempirical) formula (IV) and wherein $Cys_1$ and $Cys_2$ are Cysteines proximal to, or terminal to $(Arg)_l;(Lys)_m;(His)_n;(Orn)_o;(Xaa)_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]-trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

In this context, it is particularly preferred that the long-chain RNA molecule of the inventive dry powder composition is complexed at least partially with a cationic or polycationic compound, preferably a cationic protein or peptide. Partially means that only a part of the long-chain RNA molecule is complexed with a cationic or polycationic compound and that the rest of the long-chain RNA molecule is in uncomplexed form ("free"). Preferably the ratio of complexed long-chain RNA to free long-chain RNA is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed long-chain RNA molecule to free long-chain RNA molecule is selected from a ratio of about 1:1 (w/w).

In the context of the present invention, a particle of the dry powder composition as defined herein, may thus comprise a long-chain RNA molecule in free form or complexed by a cationic or polycationic compound. In a preferred embodiment, a particle of the inventive dry powder composition as described herein comprises or consists of long-chain RNA complexed by a cationic or polycationic compound, wherein the complex is preferably present as a nanoparticle as defined herein. As used herein, the term "nanoparticle" typically refers to a complex of the long-chain RNA molecule with a complexation agent as defined herein, preferably with a cationic or polycationic compound.

In a preferred embodiment, upon reconstitution of the dry powder in a suitable solvent, the complexed long-chain RNA molecule as described herein is present in the solvent in the form of nanoparticles. The size of the nanoparticle comprising or consisting of complexed long-chain RNA molecule after reconstitution is preferably from 50 to 500 nm, more preferably from 50 to 200 nm. In a particularly preferred embodiment, the particle size of the nanoparticle comprising or consisting of complexed long-chain RNA molecule after reconstitution is from 75 to 180 nm, more preferably from 100 to 150 nm.

Preferably, the nanoparticle comprising or consisting of complexed long-chain RNA molecule is characterized by at least one physico-chemical property. Suitable methods for determining a physico-chemical property of the nanoparticle comprising or consisting of complexed long-chain RNA molecule are known in the art. Preferably, a physico-chemical property of the nanoparticle comprising or consisting of complexed long-chain RNA molecule is determined by using a method selected from the group consisting of measurement of turbidity, dynamic light scattering (DLS), nanoparticle tracking analysis (NTA), determining the Zeta potential and micro-flow imaging (MFI). More preferably, such method is used to characterize the nanoparticles comprised in a liquid composition obtained after reconstitution of the inventive dry powder in an appropriate solvent, preferably water, more preferably water for injection.

In a preferred embodiment, a physico-chemical property of the nanoparticle comprising or consisting of complexed long-chain RNA molecule is determined by nanoparticle tracking analysis (NTA). As used herein, the term 'nanoparticle tracking analysis' or 'NTA' refers to a method for analyzing particles in a liquid that relates the rate of Brownian motion to particle size. Suitable NTA protocols are known in the art and instruments for NTA are commercially available (such as the NanoSight instruments, e.g. NanoSight LM20, NanoSight, Amesbury, UK). In preferred embodiments, the mean size, preferably the mean size as determined by NTA, of the nanoparticles comprising or consisting of complexed long-chain RNA molecule is equal to or larger than 100 nm, equal to or larger than 101 nm, equal to or larger than 102 nm, equal to or larger than 103 nm, equal to or larger than 104 nm, equal to or larger than 105 nm, equal to or larger than 106 nm, equal to or larger than 107 nm, equal to or larger than 108 nm, equal to or larger than 109 nm, equal to or larger than 110 nm, equal to or larger than 111 nm, equal to or larger than 112 nm, equal to or larger than 113 nm, equal to or larger than 114 nm, equal to or larger than 115 nm, equal to or larger than 116 nm, equal to or larger than 117 nm, equal to or larger than 118 nm, equal to or larger than 119 nm, equal to or larger than 120 nm, equal to or larger than 125 nm or equal to or larger than 130 nm. In a particularly preferred embodiment, the mean size, preferably the mean size as determined by NTA, of the nanoparticles comprising or consisting of complexed long-chain RNA molecule is equal to or larger than 110 nm, more preferably equal to or larger than 120 nm, most preferably the mean size, preferably the mean size as determined by NTA, of the nanoparticles comprising or consisting of complexed long-chain RNA molecule is equal to or larger than 130 nm. Alternatively, the mean size, preferably the mean size as determined by NTA, of the nanoparticles comprising or consisting of complexed long-chain RNA molecule is in a range from 100 nm to 200 nm, preferably from 110 nm to 150 nm.

According to a further preferred embodiment, the mode size, preferably the mode size as determined by NTA, of the nanoparticles comprising or consisting of complexed long-chain RNA molecule is equal to or larger than 90 nm, equal to or larger than 91 nm, equal to or larger than 92 nm, equal to or larger than 93 nm, equal to or larger than 94 nm, equal to or larger than 95 nm, equal to or larger than 96 nm, equal to or larger than 97 nm, equal to or larger than 98 nm, equal to or larger than 99 nm, equal to or larger than 100 nm, equal to or larger than 105 nm, equal to or larger than 110 nm, equal to or larger than 115 nm, equal to or larger than 120 nm, equal to or larger than 125 nm or equal to or larger than 130 nm. According to a particularly preferred embodiment, the mode size, preferably the mode size as determined by NTA, of the nanoparticles comprising or consisting of complexed long-chain RNA molecule is equal to or larger than 95 nm, more preferably equal to or larger than 100 nm, most preferably equal to or larger than 105 nm. Alternatively, the mode size, preferably the mode size as determined by NTA, of the nanoparticles comprising or consisting of complexed long-chain RNA molecule is preferably in a range from 95 nm to 150 nm, more preferably in a range from 100 nm to 140 nm.

In a further preferred embodiment, the D10 size, preferably the D10 size as determined by NTA, of the nanoparticles comprising or consisting of complexed long-chain RNA molecule is equal to or larger than 70 nm, equal to or larger than 71 nm, equal to or larger than 72 nm, equal to or larger than 73 nm, equal to or larger than 74 nm, equal to or larger than 75 nm, equal to or larger than 76 nm, equal to or larger than 77 nm, equal to or larger than 78 nm, equal to or larger than 79 nm, equal to or larger than 80 nm, equal to or larger than 85 nm, equal to or larger than 90 nm, equal to or larger than 95 nm, equal to or larger than 100 nm, equal to or larger than 105 nm or equal to or larger than 110 nm. It is particularly preferred that the D10 size, preferably the D10 size as determined by NTA, of the nanoparticles comprising or consisting of complexed long-chain RNA molecule is equal to or larger than 75 nm, more preferably equal to or larger than 80 nm, most preferably equal to or larger than 85 nm or 90 nm. Alternatively, the D10 size, preferably the D10 size as determined by NTA, of the nanoparticles comprising or consisting of complexed long-chain RNA molecule is in a range from 70 nm to 140 nm, more preferably in a range from 75 nm to 135 nm, most preferably in a range from 80 nm to 130 nm.

According to another embodiment, the D50 size, preferably the D50 size as determined by NTA, of the nanoparticles comprising or consisting of complexed long-chain RNA molecule is equal to or larger than 100 nm, equal to or larger than 101 nm, equal to or larger than 102 nm, equal to or larger than 103 nm, equal to or larger than 104 nm, equal to or larger than 105 nm, equal to or larger than 106 nm, equal to or larger than 107 nm, equal to or larger than 108 nm, equal to or larger than 109 nm, equal to or larger than 110 nm, equal to or larger than 115 nm, equal to or larger than 120 nm, equal to or larger than 125 nm, equal to or larger than 130 nm, equal to or larger than 130 nm or equal to or larger than 135 nm. It is particularly preferred that the D50 size, preferably the D50 size as determined by NTA, of the nanoparticles comprising or consisting of complexed long-chain RNA molecule is equal to or larger than 100 nm, more preferably equal to or larger than 105 nm, most preferably equal to or larger than 110 nm, equal to or larger than 115 nm, or equal to or larger than 120 nm. Alternatively, the D50 size, preferably the D50 size as determined by NTA, of the nanoparticles comprising or consisting of complexed long-chain RNA molecule is in a range from 100 nm to 150 nm, more preferably in a range from 105 nm to 145 nm, most preferably in a range from 110 nm to 140 nm.

According to a preferred embodiment, the D90 size, preferably the D90 size as determined by NTA, of the nanoparticles comprising or consisting of complexed long-chain RNA molecule is equal to or larger than 145 nm, equal to or larger than 146 nm, equal to or larger than 147 nm, equal to or larger than 148 nm, equal to or larger than 148 nm, equal to or larger than 149 nm, equal to or larger than 150 nm, equal to or larger than 151 nm, equal to or larger than 152 nm, equal to or larger than 153 nm, equal to or larger than 154 nm, equal to or larger than 155 nm, equal to or larger than 160 nm, equal to or larger than 165 nm, equal to or larger than 170 nm, equal to or larger than 180 nm or equal to or larger than 190 nm. It is particularly preferred that the D90 size, preferably the D90 size as determined by NTA, of the nanoparticles comprising or consisting of complexed long-chain RNA molecule is equal to or larger than 150 nm, more preferably equal to or larger than 160 nm, most preferably equal to or larger than 170 nm or 180 nm. Alternatively, the D90 size, preferably the D90 size as determined by NTA, of the nanoparticles comprising or consisting of complexed long-chain RNA molecule is in a range from 140 nm to 210 nm, more preferably in a range from 150 nm to 210 nm, most preferably in a range from 160 nm to 200 nm.

In a preferred embodiment, a physico-chemical property of the nanoparticle comprising or consisting of complexed long-chain RNA molecule is determined by dynamic light scattering (DLS). In this context, the term 'dynamic light scattering' or 'DLS' refers to a method for analyzing particles in a liquid, wherein the liquid is typically illuminated with a monochromatic light source and wherein the light scattered by particles in the liquid is detected. Due to Brownian motion, smaller particles typically result in time-dependent scattering intensity fluctuations that are distinct from those observed for larger particles. DLS can thus be used to measure particle sizes in a liquid. Suitable DLS protocols are known in the art. DLS instruments are commercially available (such as the Zetasizer Nano Series, Malvern Instruments, Worcestershire, UK). Preferably, DLS is used in the context of the present invention to determine the polydispersity index (PDI) and/or the main peak diameter of the nanoparticles comprising or consisting of complexed long-chain RNA molecule, preferably in a liquid composition obtained by reconstitution of the inventive dry powder in a suitable solvent, preferably in water, more preferably in water for injection.

According to a preferred embodiment, the polydispersity index (PDI), preferably the PDI as determined by DLS, of the nanoparticles comprising or consisting of complexed long-chain RNA molecule is equal to or larger than 0.10, equal to or larger than 0.11, equal to or larger than 0.12, equal to or larger than 0.13, equal to or larger than 0.14, equal to or larger than 0.15, equal to or larger than 0.16, equal to or larger than 0.17, equal to or larger than 0.18, equal to or larger than 0.19, equal to or larger than 0.20, equal to or larger than 0.21, equal to or larger than 0.22, equal to or larger than 0.23, equal to or larger than 0.24, equal to or larger than 0.25 or equal to or larger than 0.26. It is particularly preferred that the PDI, preferably the PDI as determined by DLS, of the nanoparticles comprising or consisting of complexed long-chain RNA molecule is equal to or larger than 0.12, more preferably equal to or larger than 0.13, most preferably equal to or larger than 0.19 or 0.21. Alternatively, the PDI, preferably the PDI as determined by DLS, of the nanoparticles comprising or consisting of complexed long-chain RNA molecule is in a range from 0.10 to 0.40, more preferably in a range from 0.13 to 0.30, most preferably in a range from 0.19 to 0.27.

It is further preferred that the main peak diameter, preferably the main peak diameter as determined by DLS, of the nanoparticles comprising or consisting of complexed long-chain RNA molecule is equal to or larger than 320 nm, equal to or larger than 325 nm, equal to or larger than 330 nm, equal to or larger than 335 nm, equal to or larger than 340 nm, equal to or larger than 345 nm, equal to or larger than 350 nm, equal to or larger than 355 nm, equal to or larger than 360 nm, equal to or larger than 365 nm, equal to or larger than 370 nm, equal to or larger than 375 nm, equal to or larger than 380 nm, equal to or larger than 385 nm, equal to or larger than 390 nm, equal to or larger than 395 nm or equal to or larger than 400 nm. It is particularly preferred that the main peak diameter, preferably the main peak diameter as determined by DLS, of the nanoparticles comprising or consisting of complexed long-chain RNA molecule is equal to or larger than 325 nm, more preferably equal to or larger than 330 nm, most preferably equal to or larger than 335 nm or 340 nm. Alternatively, the main peak diameter, preferably the main peak diameter as determined by DLS, of the nanoparticles comprising or consisting of complexed long-chain RNA molecule is in a range from 300 nm to 400 nm, more preferably in a range from 330 nm to 400 nm, most preferably in a range from 327 nm to 390 nm.

In a preferred embodiment, the Zeta potential of the nanoparticles comprising or consisting of complexed long-chain RNA molecule is determined. Methods for determining the Zeta potential are known in the art. For example, the Zeta potential of the nanoparticles comprising or consisting of complexed long-chain RNA molecule can be determined by using a Zetasizer Nano Series (Malvern Instruments, Worcestershire, UK). Preferably, the Zeta potential of the nanoparticles comprising or consisting of complexed long-chain RNA molecule is in a range from −36 mV to −50 mV, more preferably from −36 mV to −45 mV.

According to a preferred embodiment, the inventive dry powder is reconstituted in a suitable solvent, preferably in water for injection, and analyzed with respect to the concentration of particles having a certain size, preferably by micro-flow imaging (MFI). For instance, protamine-formulated RNA, which has preferably been spray-dried and reconstituted as described in the Examples 1 to 6 herein, may be analyzed by MFI as described in Example 8.3.6. In that particular embodiment, the concentration of particles having a diameter of at least 1 µm is equal to or less than 175/ml, equal to or less than 170/ml, equal to or less than 165/ml, equal to or less than 160/ml, equal to or less than 155/ml, equal to or less than 150/ml, equal to or less than 145/m1 or equal to or less than 140/ml. More preferably, the concentration of particles having a diameter of at least 2 µm is equal to or less than 35/ml, equal to or less than 32/ml, equal to or less than 31/ml, equal to or less than 30/ml, equal to or less than 29/ml, equal to or less than 28/ml, equal to or less than 27/ml, equal to or less than 26/ml or equal to or less than 25/ml.

According to another embodiment, the dry powder composition as described herein comprises a long-chain RNA, which is preferably not complexed with poly(lactide-co-glycolide) PLGA. More preferably, the dry powder composition as described herein does not comprise PLGA. Alternatively, the dry powder composition as described herein comprises a long-chain RNA, which is preferably not complexed with a compound selected from the group consisting of PLGA, poly-lactide (PLA), polyethylene imine (PEI) or poly-L-lysine (PLL). More preferably, the dry powder composition as described herein does not comprise a compound selected from the group consisting of PLGA, PLA, PEI or PLL.

According to a further embodiment, the dry powder composition as described herein comprises a long-chain RNA, which is preferably not complexed with DOTAP. More preferably, the dry powder composition as described herein does not comprise DOTAP. Even more preferably, the dry powder composition as described herein may comprise a long-chain RNA, which is preferably not complexed with a cationic lipid. More preferably, the dry powder composition as described herein does not comprise a cationic lipid.

In an alternative embodiment, the dry powder composition as described herein comprises a long-chain RNA, which is preferably not complexed with mannitol, trehalose or lactose. More preferably, the dry powder composition as described herein does not comprise mannitol, trehalose or lactose. Even more preferably, the dry powder composition as described herein may comprise a long-chain RNA, which is preferably not complexed with a carbohydrate. More preferably, the dry powder composition as described herein does not comprise a carbohydrate.

In some embodiments, the long-chain RNA of the dry powder composition as described herein is not comprised in nanoparticles or in liposomes, preferably as defined herein. Furthermore, the dry powder composition may preferably not comprise a nanoparticle or a liposome, preferably as defined herein.

In a preferred embodiment, the inventive dry powder composition comprising a long-chain RNA molecule comprises at least one further component or excipient.

In a preferred embodiment, the inventive dry powder composition comprises a solvent, preferably in the amounts as defined herein with respect to the residual moisture content of the dry powder composition. Typically, the solvent is a residue of a solvent, which was used during preparation of the dry powder composition, a residue of which may be present in the inventive dry powder composition. Preferably, the solvent contained in the inventive dry powder composition is a residue of a solvent used during preparation of the dry powder composition by using the inventive method as described herein.

In one embodiment, the solvent comprised in the dry powder composition according to the invention is suitable for use in spray drying. Preferably, a solvent is comprised in the inventive composition, in which the long-chain RNA and any other component comprised in the composition, if present, are soluble. More preferably, the solvent is volatile with a boiling point of preferably below 150° C. In addition, the solvent is preferably non-toxic. Preferably, the solvent is an aqueous solution. In the case of an organic solvent, the solvent is preferably miscible with water.

In a preferred embodiment, the solvent comprised in the dry powder composition according to the invention comprises an aequeous solution or water, preferably pyrogen-free water or water for injection (WFI). In this context, the term "water for injection" (WFI) is a term defined by standard USP 23. USP 23 monograph states that "Water for Injection (WFI) is water purified by distillation or reverse osmosis." WFI is typically produced by either distillation or 2-stage reverse osmosis. WFI typically does not contain more than 0.25 USP endotoxin units (EU) per ml. Endotoxins are a class of pyrogens that are components of the cell wall of Gram-negative bacteria (the most common type of bacteria in water), preferably in an action limit of 10 cfu/100 ml. The microbial quality may be tested by membrane filtration of a 100 ml sample and plate count agar at an incubation temperature of 30 to 35 degrees Celsius for a 48-hour period. The chemical purity requirements of WFI are typically the same as of PW (purified water).

As a further excipient, the dry powder composition according to the invention may comprise a buffer, preferably selected from a buffer as defined herein, e.g. a buffer containing 2-hydroxypropanoic acid, preferably including at least one of its optical isomers L-(+)-lactic acid, (S)-lactic acid, D-(−)-lactic acid or (R)-lactic acid, more preferably its biologically active optical isomer L-(+)-lactic acid, or a salt or an anion thereof, preferably selected from sodium-lactate, potassium-lactate, or $Al_3^+$-lactate, $NH_4^+$-lactate, Fe-lactate, Li-lactate, Mg-lactate, Ca-lactate, Mn-lactate or Ag-lactate, or a buffer selected from Ringer's lactate (RiLa), lactated Ringer's solution (main content sodium lactate, also termed "Hartmann's Solution" in the UK), acetated Ringer's solution, or ortho-lactate-containing solutions (e.g. for injection purposes), or lactate containing water. A buffer as defined herein may also be a mannose containing buffer, an isotonic buffer or solution, preferably selected from isotonic saline, a lactate or ortho-lactate-containing isotonic solution, a isotonic buffer or solution selected from phosphate-buffered saline (PBS), TRIS-buffered saline (TBS), Hank's balanced salt solution (HBSS), Earle's balanced salt solution (EBSS), standard saline citrate (SSC), HEPES-buffered saline (HBS), Grey's balanced salt solution (GBSS), or normal saline (NaCl), hypotonic (saline) solutions with addition of glucose or dextrose, or any solution as defined herein, etc. These isotonic buffers or solutions are preferably prepared as defined herein or according to protocols well known in the art for these specific isotonic buffers or solutions. In this context, a buffer or, in particular, a residue thereof, may be comprised in the dry powder composition according to the invention, more preferably an aqueous (isotonic solution or aqueous) buffer, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, NaHCO$_3$, Na$_2$SO$_4$, examples of the optional potassium salts include e.g. KCl, KI, KBr, K$_2$CO$_3$, KHCO$_3$, K$_2$SO$_4$, and examples of calcium salts include e.g. CaCl$_2$, CaI$_2$, CaBr$_2$, CaCO$_3$, CaSO$_4$, Ca(OH)$_2$. Typically, the salts are present in such a buffer in a concentration of at least 50 mM sodium chloride (NaCl), at least 3 mM potassium chloride (KCl) and at least 0.01 mM calcium chloride (CaCl$_2$). Furthermore, organic anions of the aforementioned cations may be contained in the buffer. According to a more preferred embodiment, the buffer may contain salts selected from sodium chloride (NaCl), calcium chloride (CaCl$_2$) and optionally potassium chloride (KCl), wherein further anions may be present in addition to the chlorides. CaCl$_2$ may also be replaced therein by another salt like KCl.

According to a particularly preferred embodiment, the inventive dry powder composition, may be reconstituted in a solvent or a buffer as defined herein, preferably as defined above. For example, the inventive dry powder composition may be reconstituted in water, Ringer Lactate solution, a buffer as defined above, or a buffer containing mannose, to obtain the desired salt concentration or alternatively the desired buffer conditions. The reconstitution of the dry powder composition is carried out in WFI (water for injection), if the dry powder composition was prepared from a long-chain RNA molecule dissolved in Ringer Lactate solution (optionally comprising further components), which represents an isotonic solution for injection. In a particularly preferred embodiment, the dry powder composition is reconstituted in an isotonic solution, preferably as defined herein, more preferably in Ringer Lactate, especially if the dry powder composition was prepared from a long-chain RNA molecule dissolved in water, preferably WFI (wherein the water optionally comprises further components).

In a preferred embodiment, the dry powder composition according to the invention does not comprise a lipid compound.

The inventive dry powder composition may further comprise any type of suitable component, which is compatible with the long-chain RNA molecule. As used herein, the term 'component' preferably comprises any additive or excipient, preferably a pharmaceutically acceptable excipient that does preferably not cause or enhance degradation of the long-chain RNA molecule. Such a component may further be in any state, such as liquid, gel-like, solid or semi-solid. A component is preferably selected from the group consisting of cryoprotectants, lyoprotectants, bulking agents, preservatives, antioxidants, antimicrobial agents, colorants, carriers, fillers, film formers, redispersants and disintegrants. Moreover, the inventive dry powder composition may also comprise excipients, such as defoamers, surfactants, viscosity enhancing agents, force control agents or the like.

Preferably, the inventive dry powder composition comprises at least one component selected from a cryoprotectant, a lyoprotectant or a bulking agent. In this context, cryoprotectants are understood as excipients, which allow influencing the structure of a frozen material and/or the eutectical temperature of the mixture. Lyoprotectants are typically excipients, which partially or totally replace the hydration sphere around a molecule and thus prevent catalytic and hydrolytic processes. A bulking agent (e.g. a filler) is any excipient compatible with the long-chain RNA molecule, which may be comprised in the inventive composition. As used herein, a bulking agent may be used for increasing the volume and/or the mass of the inventive composition. In addition, a bulking agent may also protect the long-chain RNA molecule from degradation.

As a particularly preferred component, the inventive dry powder composition may additionally contain at least one suspending agent, preferably mannit.

As a further component, the inventive dry powder composition may additionally contain at least one component selected, e.g., from proteins, amino acids, alcohols, carbohydrates, mannose, mannit, metals or metal ions, surfactants, polymers or complexing agents, buffers, etc., or a combination thereof.

In the context of the present invention, one preferred component may also be selected from the group of amino acids. Such group may comprise, without being limited thereto, any naturally occurring amino acid, including alanine, cysteine, aspartic acid, glutamic acid, phenylalanine, glycine, histidine, isoleucine, lysine, leucine, methionine, asparagine, pyrrolysine, proline, glutamine, arginine, serine, threonine, selenocysteine, valine, tryptophan, and tyrosine, more preferably glycine, arginine, and alanine. Cryoprotectants and/or lyoprotectants selected from the group of amino acids may additionally comprise any modification of a naturally occurring amino acid as defined above.

Furthermore, in the context of the present invention, a further component may be selected from the group of alcohols. Such group may comprise, without being limited thereto, any alcohol suitable for the preparation of a pharmaceutical composition, preferably, without being limited thereto, mannitol, polyethyleneglycol, polypropyleneglycol, sorbitol, etc.

Additionally, in the context of the present invention, a further component may be selected from the group of (free) carbohydrates. In general, a carbohydrate, such as a sugar, can act, for example, as a bulking agent, enhance cell targeting (e.g., galactose, lactose), open cellular junctions (e.g., mannitol), and modulate, for instance, the powder's flowability by altering particle density. Such group of (free) carbohydrates may comprise, without being limited thereto, any (free) carbohydrate, suitable for the preparation of a pharmaceutical composition, preferably, without being limited thereto, (free) monosaccharides, such as e.g. (free) glucose, (free) fructose, (free) galactose, (free) sorbose, (free) mannose ("free" preferably means unbound or unconjugated, e.g. the mannose is not covalently bound to the long-chain RNA molecule, or in other words, the mannose is unconjugated, preferably with respect to the long-chain RNA molecule), etc., and mixtures thereof; disaccharides, such as e.g. lactose, maltose, sucrose, trehalose, cellobiose, etc., and mixtures thereof; polysaccharides, such as raffinose, melezitose, maltodextrins, dextrans, starches, etc., and mixtures thereof; and alditols, such as mannitol, xylitol, maltitol, lactitol, xylitol sorbitol, pyranosyl sorbitol, myo-inositol, etc., and mixtures thereof. Examples of sugars that are preferably used in the composition according to the invention include lactose, sucrose or trehalose. Generally, a sugar that is preferred in this context, has a high water displacement activity and a high glass transition temperature. Furthermore, a sugar suitable for use in the composition is preferably hydrophilic but not hygroscopic. In addition, the sugar preferably has a low tendency to crystallize, such as trehalose. Trehalose is particularly preferred.

In an alternative embodiment, the dry powder composition may comprise a cryoprotectant, which is preferably not selected from lactose or trehalose. More preferably, the cryoprotectant is not a carbohydrate.

The weight ratio of the long-chain RNA molecule in the composition to the carbohydrate component, preferably a sugar, more preferably trehalose, in the composition is preferably in the range from about 1:2.000 to about 1:10, more preferably from about 1:1,000 to about 1:100. Most preferably, the weight ratio of the long-chain RNA molecule in the composition to the carbohydrate excipient, preferably a sugar, more preferably trehalose, in the composition is in the range from about 1:250 to about 1:10 and more preferably in the range from about 1:100 to about 1:10 and most preferably in the range from about 1:100 to about 1:50.

In preferred embodiment, the dry powder composition according to the present invention comprises at least 50% (w/w), preferably at least 70% (w/w), at least 80% (w/w), at least 90% (w/w), or at least 95% (w/w) of a carbohydrate component, preferably a sugar, more preferably trehalose.

In a particularly preferred embodiment, the inventive dry powder composition comprises trehalose. More preferably, trehalose is present in the inventive dry powder composition in a relative amount of about 5% to about 99.5% (w/w), preferably in a relative amount of about 20% to about 98% (w/w), more preferably in a relative amount of about 50% to about 95% (w/w), even more preferably in a relative amount of about 70 to about 99% (w/w), and most preferably in a relative amount of about 75 to about 90% (w/w). Preferably, the relative amount of trehalose in the inventive dry powder composition is at least 30% (w/w), at least 40% (w/w), at least 50% (w/w), at least 60% (w/w), at least 70% (w/w), at least 80% (w/w), at least 90% (w/w) or at least 95% (w/w).

In the context of the present invention, a further suitable component may also be selected from the group of proteins. Such group may comprise, without being limited thereto, proteins such as albumin, gelatine, therapeutically active proteins, antibodies, antigens, or any further protein encoded by the long-chain RNA molecule as defined herein.

A component, which may be contained in the inventive dry powder composition may be selected from the group of metals or metal ions, typically comprising, without being limited thereto, metals or metal ions or salts selected from alkali metals, including members of group 1 of the periodic table: lithium (Li), sodium (Na), potassium (K), rubidium (Rb), caesium (Cs), and francium (Fr), and their (monovalent) metal alkali metal ions and salts; preferably lithium (Li), sodium (Na), potassium (K), and their (monovalent) metal alkali metal ions and salts;
alkaline earth metals, including members of group 2 of the periodic table: beryllium (Be), magnesium (Mg), calcium (Ca), strontium (Sr), barium (Ba) and radium (Ra), and their (divalent) alkaline earth metal ions and salts; preferably magnesium (Mg), calcium (Ca), strontium (Sr), barium (Ba) and their (divalent) alkaline earth metal ions and salts;
transition metals, including members of groups 3 to 13 of the periodic table and their metal ions and salts. The transition metals typically comprise the 40 chemical elements 21 to 30, 39 to 48, 71 to 80, and 103 to 112. The name transition originates from their position in the periodic table of elements. In each of the four periods in which they occur, these elements represent the successive addition of electrons to the d atomic orbitals of the atoms. In this way, the transition metals represent the transition between subgroup 2 elements and subgroup 12 (or 13) elements. Transition metals in the context of the present invention particularly comprise members of subgroup 3 of the periodic table: including Scandium (Sc), Yttrium (Y), and Lutetium (Lu), members of subgroup 4 of the periodic table: including Titan (Ti), Zirconium (Zr), and Hafnium (Hf), members of subgroup 5 of the periodic table: including Vanadium (V), Niobium (Nb), and Tantalum (Ta), members of subgroup 6 of the periodic table: including Chrome (Cr), Molybdenum (Mo), and Tungsten (W), members of subgroup 7 of the periodic table: including Manganese (Mn), Technetium (Tc), and Rhenium (Re), members of subgroup 8 of the periodic table: including Iron (Fe), Ruthenium (Ru), and Osmium (Os), members of subgroup 9 of the periodic table: including Cobalt (Co), Rhodium (Rh), and Iridium (Ir), members of subgroup 10 of the periodic table: including Nickel (Ni), Palladium (Pd), and Platin (Pt), members of subgroup 11 of the periodic table: including Copper (Cu), Silver (Ag), and Gold (Au), members of subgroup 12 of the periodic table: including Zinc (Zn), Cadmium (Cd), and Mercury (Hg); preferably members of period 4 of any of subgroups 1 to 12 of the periodic table: including Scandium (Sc), Titanium (Ti), Vanadium (V), Chromium (Cr), Manganese (Mn), Iron (Fe), Cobalt (Co), Nickel (Ni), Copper (Cu) and Zinc (Zn) and their metal ions and salts;
earth metals or members of the boron group, including members of group 3 of the periodic table: including Boron (B), Aluminium (Al), Gallium (Ga), Indium (In) and Thallium (Tl) and their metal ions and salts; preferably Boron (B) and Aluminium (Al) and their metal ions and salts;
metalloids or semi metals: including Boron (B), Silicon (Si), Germanium (Ge), Arsenic (As), Antimony (Sb), Tellurium (Te). and Polonium (Po), and their semi metal ions and salts; preferably Boron (B) and Silicon (Si) and their semi metal ions and salts;

In the context of the present invention, a further component may be selected from the group of surfactants may comprise, without being limited thereto, any surfactant, preferably any pharmaceutically acceptable surfactant, which is preferably suitable for spray drying. More preferably, without being limited thereto, the surfactant is selected from the group consisting of Tween, e.g. Tween 80 (0.2%), Pluronics, e.g. Pluronic L121 (1.25%), Triton-X, SDS, PEG, LTAB, Saponin, Cholate, etc.

As another component, the inventive dry powder composition may additionally contain one or more compatible solid or liquid fillers or diluents or encapsulating compounds, which are preferably suitable for administration to a patient to be treated. The term "compatible" as used here means that these constituents are capable of being mixed with the long-chain RNA molecule (free or in a complex with a cationic or polycationic compound), as defined according to the present invention, in such a manner that no interaction occurs, which would substantially reduce the integrity or biological activity of the long-chain RNA molecule, under typical use conditions. Pharmaceutically acceptable carriers, fillers and diluents must, of course, have sufficiently high purity and sufficiently low toxicity to make them suitable for administration to a person to be treated. Some examples of compounds, which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

In addition, the dry powder composition according to the invention may optionally contain further excipients or agents, such as stabilizers, for example EDTA, Tween, benzoic acid derivatives or RNAse inhibitors. Preferably, the dry powder composition may further comprise any type of component or additive, which is compatible with the long-chain RNA molecule. Such an excipient is preferably selected from the group consisting of preservatives, antioxidants, antimicrobial agents, colorants, carriers, fillers, film formers, redispersants and disintegrants. Moreover, the dry powder composition may also comprise a component or additive, preferably in very small amounts, that were added during the manufacturing process, such as defoamers, surfactants, viscosity enhancing agents, force control agents or the like.

In a preferred embodiment, the dry powder composition of the invention is obtained by the method as described herein.

As explained herein, the dry powder composition according to the invention is particularly suitable as storage-stable form of a long-chain RNA molecule. The inventors have surprisingly found that the storage stability of the long-chain RNA molecule in the dry powder composition is excellent and the long-chain RNA molecule remains functional after extended storage periods. The storage stability of the long-chain RNA molecule is typically determined through determination of the relative (structural) integrity and the biological activity after a given storage period, e.g. via time-course in vitro expression studies.

The relative integrity is preferably determined as the percentage of full-length RNA (i.e. non-degraded long-chain RNA) with respect to the total amount of RNA (i.e. long-chain RNA and degraded RNA fragments (which appear as smears in gel electrophoresis)), preferably after deduction of the LOD (3×background noise), for example, by using the software QuantityOne from BioRad.

The dry powder composition according to the invention thus provides the advantageous characteristics of a powder and the potential of such a composition for, e.g. packaging and dosage, while it also allows significantly longer storage at temperatures from −80° C. to 60° C. than the corresponding RNAs in WFI or other injectable solutions. Particularly, it can be stored at room temperature, which simplifies shipping and storage. Preferably, the dry powder composition is stored with or without shielding gas. In one embodiment, single doses of the dry powder composition are packaged and sealed. Alternatively, multiple doses can be packaged in one packaging unit. Single dose packaging in blisters or capsules is preferably used in order to prevent cross-contamination.

Preferably, the relative integrity is at least 70%, more preferably at least 75%, at least 80%, at least 85%, at least 90% or at least 95% after storage at room temperature for preferably at least one week, more preferably for at least one month, even more preferably for at least 6 months and most preferably for at least one year.

Further preferably, the biological activity of the long-chain RNA molecule of the dry powder composition after storage at room temperature, preferably as defined above with respect to the relative integrity of the long-chain RNA molecule, is preferably at least 70%, more preferably at least 75%, at least 80%, at least 85%, at least 90% or at least 95% of the biological activity of the freshly prepared long-chain RNA molecule. The biological activity is preferably determined by analysis of the amounts of protein expressed from reconstituted RNA and from freshly prepared RNA, respectively, e.g. after transfection into a mammalian cell line. Alternatively, the biological activity may be determined by measuring the induction of an (adaptive or innate) immune response in a subject.

In a further aspect of the invention, a method is provided that allows preparing a storage form of a long-chain RNA molecule, preferably a long-chain RNA in particulate form as described herein, wherein a liquid comprising the RNA molecule is provided and wherein the liquid is dried by spray-drying. In one embodiment, the invention concerns a method for drying a liquid comprising a long-chain RNA molecule.

With respect to the following description of the inventive method, it is noted that the definitions and specifications provided above with respect to the inventive dry powder composition may likewise apply to the inventive method. In particular, the description of the long-chain RNA molecule and further components of the dry powder composition apply to the inventive method as well. In addition, further definitions may apply to the inventive method as specifically indicated in the following.

In a preferred embodiment, the invention concerns a method for preparing a dry powder comprising a long-chain RNA molecule, wherein the method comprises the following steps:

a) providing a liquid comprising the long-chain RNA molecule,
b) drying the liquid provided in step a) by spray-drying.

The inventors found that a storage form of a long-chain RNA molecule may be obtained by the method as described herein. In particular, the inventors found that—by using the method according to the invention—a dry powder comprising a long-chain RNA molecule can be obtained. Advantageously, the method according to the invention is suitable for application at an industrial scale. In addition, the invention provides a method that can be carried out by the skilled person using standard equipment, thus providing a cost- and time-effective solution. Moreover, the method can be carried out in bulk as well as continuously. The storage form, preferably the long-chain RNA in particulate form, obtained by using the method according to the invention therefore represents an effective means for extending the stability of long-chain RNA as an API (active pharmaceutical ingredient), especially during storage at a variety of different temperatures and in different packaging formats.

In step a) of the method according to the invention, a liquid is provided that comprises a long-chain RNA molecule. The long-chain RNA molecule comprised in the liquid provided in step a) of the inventive method is characterized by any feature or any combination of features described herein with respect to the long-chain RNA molecule that is comprised in the inventive dry powder composition.

Typically, the liquid in step a) of the method according to the invention is provided by diluting or dissolving the long-chain RNA molecule in a suitable solvent. The solvent is preferably a solvent suitable for use in spray drying. Preferably, a solvent is used, in which the long-chain RNA and any other component, if present, are soluble. Suitable solvents are described above with respect to the inventive dry powder composition. The liquid in step a) of the inventive method preferably comprises the long-chain RNA molecule and a solvent or buffer as described above with respect to the inventive dry powder composition. Preferably, step a) of the inventive method comprises dissolving or diluting the long-chain RNA molecule as defined herein in a solvent or buffer as defined herein, preferably in an aqueous solution, such as Ringer Lactate, or water, more preferably pyrogen-free water or WFI.

In a further preferred embodiment, the liquid comprising the long-chain RNA molecule comprises at least one further component, preferably as described herein with respect to the dry powder composition disclosed herein. In particular, the liquid provided in step a) of the inventive method preferably comprises a further component selected from the group consisting of buffers, cryoprotectants, lyoprotectants, bulking agents, suspending agents, proteins, amino acids, alcohols, carbohydrates, metals, metal ions, salts, surfactants, fillers, diluents, carriers, glidants, vegetable oils, polyols, encapsulating compounds, stabilizers, preservatives, antioxidants, antimicrobial agents, colorants, film formers, redispersants, disintegrants, defoamers, viscosity enhancing agents and force control agents, wherein the respective component is preferably as defined above with respect to the inventive dry powder composition.

The long-chain RNA molecule as defined herein may be present in the liquid provided in step a) of the inventive method in free form (as "naked RNA") and/or as a complex with a polycationic or cationic compound, preferably as described herein. The long-chain RNA molecule as defined herein and a cationic or polycationic compound may be comprised in the liquid provided in step a), either as a complex, preferably in the form of a nanoparticle as defined herein, or both in free form, i.e. in solution without being in a complex with each other. The preparation of RNA complexes with complexation agents, preferably with polycationic or cationic compounds, is known in the art and is preferably carried out as described in WO2010/037539 or WO2011/026641, the entire disclosure of which is herewith incorporated by reference.

In a particularly preferred embodiment, the liquid provided in step a) of the inventive method comprises a complexation agent, preferably as defined herein, more preferably a cationic or polycationic compound as defined herein, such as protamine, nucleoline, spermin, spermidine, oligoarginines as defined above, such as $Arg_7$, $Arg_8$, $Arg_9$, $Arg_7$, $H_3R_9$, $R_9H_3$, $H_3R_9H_3$, $YSSR_9SSY$, $(RKH)_4$, $Y(RKH)_2R$, etc. The complexation agent, preferably a cationic or polycationic compound as defined herein, is preferably present in the liquid provided in step a) in free form (in solution) or in a complex with the long-chain RNA molecule. Protamine is particularly preferred and is preferably comprised in the liquid provided in step a) of the method at a concentration in a range from 0.01 g/l to 10 g/l, from 0.05 g/l to 5 g/l, or from 0.05 g/l to 2 g/l. More preferably, the concentration of protamine in the liquid provided in step a) of the method is in a range from 0.05 g/l to 3 g/l or from 0.1 to 1 g/l.

In a preferred embodiment, the liquid provided in step a) further comprises lactate, wherein the lactate concentration is preferably in the range of about 3 mM to about 300 mM, preferably in the range of about 5 mM to about 200 mM, more preferably in the range of about 10 mM to about 150 mM, even more preferably about 15 mM to about 35 mM, and most preferably 20 mM to about 31 mM. Alternatively, the liquid provided in step a) of the method typically comprises a Ringer's lactate concentration (or a concentration of any of the afore mentioned lactate containing solutions) e.g. in the range of about 10% (w/w) to about 100% (w/w), e.g. in the range of about 20% (w/w) to about 100% (w/w), in the range of about 30% (w/w) to about 100% (w/w), in the range of about 40% (w/w) to about 100% (w/w), in the range of about 50% (w/w) to about 90% (w/w), preferably in the range of about 60% (w/w) to about 90% (w/w), more preferably in the range of about 70% (w/w) to about 90% (w/w), e.g. about 80% (w/w), of Ringer's lactate (or the afore mentioned lactate containing solution). In this context, Ringer's lactate (100% (w/w)) is typically defined as a solution comprising 131 mM $Na^+$, 5.36 mM $K^+$, 1.84 mM $Ca^{2+}$, and 28.3 mM Lactate).

In another embodiment, the liquid provided in step a) of the inventive method does not comprise a lipid compound.

As a particularly preferred component, the liquid provided in step a) of the method may additionally contain at least one suspending agent, preferably mannit, preferably in a concentration of about 1 to 15% (w/w), more preferably in a concentration of about 3 to 10% (w/w), and even more preferably in a concentration of about 4 to 6% (w/w).

In a further embodiment, the liquid provided in step a) of the method comprises a carbohydrate component, preferably a sugar, more preferably trehalose. In a preferred embodiment, a carbohydrate component, preferably a sugar, more preferably trehalose is present in the liquid provided in step a) of the method at a concentration of about 0.01 to about 20% (w/w), preferably in a concentration of about 0.01 to about 15% (w/w), more preferably in a concentration of about 0.1 to about 10% (w/w), even more preferably in a concentration of about 0.5 to about 10% (w/w), and most preferably in a concentration of about 2.5 to about 7.5% (w/w), e.g. at a concentration of about 4 to about 7% (w/w), such as about 5% (w/w).

The pH of the liquid provided in step a) of the method may be in the range of about 4 to 8, preferably in the range of about 6 to about 8, more preferably from about 7 to about 8.

Preferably, the liquid provided in step a) of the method contains the herein defined contents, optional components, additives, etc. in such a concentration so as to lead to an osmolarity comparable to that of blood plasma. In this context, the term "osmolarity" is typically to be understood as a measure of all contents, optional components, additives, etc. of the liquid as defined herein. More precisely, osmolarity is typically the measure of solute concentration, defined as the number of osmoles (Osm) of all solubilized contents, optional components, additives, etc. per liter (l) of solution (osmol/l or osm/l). In the present context, the liquid provided in step a) of the method may comprise an osmolarity preferably in the range of about 200 mosmol/l to about 400 mosmol/l, more preferably in the range of about 250 mosmol/l to about 350 mosmol/l, even more preferably in the range of about 270 mosmol/l to about 330 mosmol/l or in the range of about 280 mosmol/l to about 320 mosmol/l, or in the range of about e.g. about 290 mosmol/l to about 310 mosmol/l, e.g. about 295 mosmol/l, about mosmol/l, about 296 mosmol/l, about 297 mosmol/l, about 298 mosmol/l, about 299 mosmol/l, about, about 300 mosmol/l, about 301 mosmol/l, about 302 mosmol/l, about 303 mosmol/l, about 304 mosmol/l, about 305 mosmol/l, about 306 mosmol/l, about 307 mosmol/l, about 308 mosmol/l.

The method according to the present invention further comprises a step b), wherein the liquid provided in step a) of the method is dried by spray-drying.

As used herein, the term 'spray-drying' typically relates to a process that involves breaking up a liquid into small droplets (atomization) and rapidly removing solvent from the droplets in a spray-drying apparatus, where there is a strong driving force for evaporation of solvent from the droplets, which provide a favourable surface to mass ratio. The strong driving force for solvent evaporation is generally provided by a high surface to mass ratio of the droplets and by maintaining the partial pressure of solvent in the spray-drying apparatus well below the vapor pressure of the solvent at the temperature of the drying droplets. This may be achieved, for example, by maintaining the pressure in the spray-drying apparatus at a partial vacuum or by mixing the droplets with a warm drying gas or a combination of both. As a result of the spray-drying process, particles, preferably dry particles, more preferably in the form of a dry powder composition, are typically obtained.

The method according to the invention may be carried out in bulk or as a continuous process. In a preferred embodiment, the method is carried out as a continuous process. In particular, the spray-drying process may be carried out in bulk or as a continuous process in the context of the inventive method. Most preferably, the spray-drying process is carried out in a continuous process.

Preferably, the liquid provided in step a) of the method is used as liquid feed in a spray-drying process.

Typically, the liquid comprising the long-chain RNA molecule, which is provided in step a), is first broken up into a plurality of small droplets that are preferably suspended in a gas or a gas mixture, such as air. The obtained mixture of droplets and gas is typically referred to as 'spray' or 'fog'. The process of breaking up the liquid feed into droplets is known as 'atomization' and may be carried out using any suitable device known in the art (atomizer). Various types of atomizers are known in the art, which are suitable for being used in the inventive method, such as rotary atomizers, pressure nozzles, two-fluid nozzles, fountain nozzles, ultrasonic nebulizers and vibrating orifice aerosol generators.

In one embodiment, a rotary atomizer is used as atomizer in the spray-drying. Rotary atomizers exploit the energy of high-speed rotation to produce fine droplets. The liquid feed is introduced into a reservoir, typically in the center of the rotary wheel.

According to a preferred embodiment, a two-fluid nozzle is used in the spray-drying process. Two-fluid nozzles combine two fluids, where one fluid is typically the liquid feed to be dried and the second fluid is typically a compressed gas (e.g. air, nitrogen or $CO_2$ at, for example, 0.1 to 7 bar). The energy of the compressed gas is used to atomize the liquid feed. Once the liquid feed is atomized, the produced spray droplets are usually mixed with a drying gas stream, allowing the liquid to quickly evaporate. The rapid evaporation typically results in a cooling effect, so that the dried particles do not reach the drying air temperature, which is particularly advantageous if heat sensitive material is dried.

In a preferred embodiment, a pressure nozzle is used as atomizer. Preferably, a pressure nozzle is used, which comprises a swirl chamber, causing the liquid passing through them to rotate. Preferably, a pressure nozzle is used as atomizer, wherein the nozzle pressure is preferably not higher than about 1 bar, more preferably not higher than about 0.7 bar, not higher than about 0.5 bar or not higher than about 0.3 bar. Preferably, the nozzle pressure is in a range from about 1 to about 0.1 bar, more preferably in a range from about 0.7 to about 0.3 bar. In a particularly preferred embodiment, the nozzle pressure is not higher than about 0.3 bar.

In the context of the present invention, an atomizer is preferably used that produces droplets, which are preferably characterized by a mass median aerodynamic diameter (MMAD), preferably as defined herein, of at least 0.3 μm. Alternatively, the MMAD of the droplets according to the invention is at least 1, 2, 3, 4, 5, 6, 7, 8, 9, 10, 15, 20, 25, 30, 35, 40, 45 or 50 μm. Preferably, the MMAD of the droplets is equal to or less than 1,500, 1,250, 1,000, 750, 600, 500, 400, 300, 200 or 100 μm. Further preferably, the MMAD of the droplets may be in a range from 0.5 μm to 2,000 μm, from 1 μm to 1,000 μm, from 2 μm to 500 μm or from 2 μm to 200 μm. In a preferred embodiment, the MMAD of the droplets is at least 1 μm or in the range from 1 to 200 μm. In a particularly preferred embodiment, the MMAD of the droplets is at least 3 μm, at least 5 μm or at least 20 μm.

Preferably, the droplet size distribution is narrow, i.e. the size of the individual droplets that are formed by the atomizer is relatively uniform. More preferably, the droplets formed by the atomizer are characterized by using the span of the droplet size distribution as a parameter. Therein, the span (for a volume weighted distribution) is defined as outlined above with respect to the particle size of the inventive dry powder composition. In a preferred embodiment, the droplet size distribution is characterized by a low span value, which preferably results in a narrow particle size distribution in the dry powder composition. Typically, a narrow droplet size distribution after atomization results in increased flowability of the resulting dry powder. Preferably, the span of the droplets formed by the atomizer is equal to or less than 5, more preferably equal to or less than 4, and even more preferably equal to or less than 3. In a particularly preferred embodiment, the particle size distribution of the dry powder composition according to the invention is characterized by a span of less than about 2 or less than about 1.5.

In a preferred embodiment, atomization of the liquid feed results in spherical droplets. As used herein, the term "spherical" comprises not only geometrically perfect spheres, but also more irregular shapes, such as spheroidal, elipsoid, oval or rounded droplet. Waddell's sphericity $\psi$ (herein also referred to as "sphericity" or "circularity") may be calculated, e.g. by using the following equation $$\psi = \frac{\text{surface area of sphere of equal volume to the droplet}}{\text{surface area of the droplet}}$$

In a preferred embodiment, a droplet formed by atomization of the liquid feed is characterized by a sphericity of at least 0.7, preferably at least 0.75, at least 0.8, at least 0.85, at least 0.9, at least 0.95 or 1. Preferably, the atomizer generates a plurality of droplets comprising at least one droplet with a sphericity in the range from 0.7 to 1, more preferably in the range from 0.8 to 1, from 0.85 to 1, or from 0.9 to 1.

It is further preferred that the average sphericity of the droplets, which are formed by the atomizer, is at least 0.7, preferably at least 0.75, at least 0.8, at least 0.85, at least 0.9, at least 0.95 or 1. Preferably, the average sphericity of the droplets, which are formed by the atomizer, is in the range from 0.7 to 1, more preferably in the range from 0.8 to 1, from 0.85 to 1, or from 0.9 to 1.

Alternatively, the sphericity of those droplets that have a particle size (i.e. droplet size) equal to Dv50 in the droplet size distribution as defined herein is at least 0.7, preferably at least 0.75, at least 0.8, at least 0.85, at least 0.9, at least 0.95 or 1. Preferably, the sphericity of those droplets that have a particle size equal to Dv50 as defined herein is in the range from 0.7 to 1, more preferably in the range from 0.8 to 1, from 0.85 to 1, or from 0.9 to 1. Even more preferably, those droplets that have a particle size equal to Dv90 as defined herein have a sphericity of at least 0.7, preferably of at least 0.75, at least 0.8, at least 0.85, at least 0.9, at least 0.95 or 1. Preferably, the sphericity of those droplets that have a particle size equal to Dv90 as defined herein is in the range from 0.7 to 1, more preferably in the range from 0.8 to 1, from 0.85 to 1, or from 0.9 to 1.

Further preferably, the average sphericity of those droplets that have a particle size equal to or lower than Dv50 as defined herein is at least 0.7, preferably at least 0.75, at least 0.8, at least 0.85, at least 0.9, at least 0.95 or 1. Preferably, the average sphericity of those droplets that have a particle size equal to or lower than Dv50 as defined herein is in the range from 0.7 to 1, more preferably in the range from 0.8 to 1, from 0.85 to 1, or from 0.9 to 1. Even more preferably, the average sphericity of those droplets that have a particle size equal to or lower than Dv90 as defined herein is at least 0.7, preferably of at least 0.75, at least 0.8, at least 0.85, at least 0.9, at least 0.95 or 1. Preferably, the average sphericity of those droplets that have a particle size equal to or lower than Dv90 as defined herein is in the range from 0.7 to 1, more preferably in the range from 0.8 to 1, from 0.85 to 1, or from 0.9 to 1.

In a preferred embodiment, the droplets formed by the atomizer are dried by evaporation of the solvent from the droplets. Typically, this takes place in a drying chamber, which may be of any shape and which may consist of one or more chambers. Preferably, the droplets are contacted with a gas stream that is preferably capable of absorbing, at least partially, the solvent that evaporates from the droplets. The gas stream is preferably introduced into the drying chamber via an inlet, such as a disperser, which is preferably located in the upper half of the drying chamber, more preferably in the vicinity of the atomizer, thus allowing rapid mixing of the drying gas and the droplets. The gas stream leaves the drying chamber through an outlet, which is preferably located at the bottom of the drying chamber. In a preferred embodiment, the drying chamber comprises a cone-shaped part, wherein the tip of the cone comprises the outlet, preferably for the drying gas as well as for dried particles.

Preferably, the characteristics of the drying chamber are matched with, amongst others, the atomizer that is used. In order to ensure uniform product quality, the droplets preferably contact a surface only when they are sufficiently dry. Spray-drying devices that use centrifugal atomizer typically require relatively larger diameter vessels, but less cylinder height for optimal drying. Spray-drying devices that use pressure nozzles usually require relatively small diameters with larger cylinder height for sufficient drying. The dry powder composition is preferably collected at the bottom of the drying chamber that is preferably designed as a cone. In the center of the cone area, the outlet of the gas-stream is preferably positioned, where cool and moist air is removed from the drying chamber. Such a design of the cone and outlet is acting as a cyclone separator and leads to an accumulation of the dry powder composition at the bottom of the drying chamber. Cyclonic separation is preferably used to separate dry particles or fine droplets from the drying gas, preferably without the use of filters, through vortex separation. To this end, a high speed rotating flow is preferably established within a cylindrical or conical container, the cyclone. Typically, drying gas flows in a helical pattern, from the top (wide end) of the cyclone to the bottom (narrow) end before exiting the cyclone in a straight stream through the center of the cyclone and out the top. Larger or denser particles in the rotating stream do not follow the tight curve of the stream, but strike the outside wall and fall to the bottom of the cyclone, where they can be collected. Alternatively, a filter, e.g. a bag filter or a combination of a cyclone separator and a filter may be used for separation.

Depending on the type of flow, i.e. the relative positions of atomizer and drying gas inlet or, respectively, the relative movement of the spray and the drying gas, several types of spray-drying devices may be distinguished, all of which may be used in the method according to the invention. In a preferred embodiment the spray-drying device is set up as a co-current flow device (spray and drying gas move into the same directions), as a counter-current flow device (spray and drying gas move into opposite directions) or as a mixed flow device (co-current and counter-current flow combined). In a particularly preferred embodiment, the spray-drying device is a co-current flow device.

Moreover, common spray-drying devices may be categorized depending on the type of air cycle that is used. A spray-drying device as used herein is preferably an open cycle device (drying air that enters the system through the inlet is exhausted through the outlet into the atmosphere) or a closed cycle device (drying air that enters the system through the inlet, exits the system via the outlet and is reused). A closed cycle device is preferably employed, if a drying gas is used that should not accumulate in the facility, where the device is located (such as nitrogen or $CO_2$), and/or if toxic substances are released from the drying material.

The spray-drying device preferably reduces the residual moisture content of the composition to the desired level, preferably as defined herein, in one pass through the system. If the moisture content of the product after one cycle is higher than desired, the moisture content of the powder may be further reduced by a second drying stage (or several of those) until the desired residual moisture content of the product is achieved.

An example of a spray-drying apparatus is shown in FIG. 1, which further illustrates the principle of spray-drying. Liquid input stream (A) is sprayed through a nozzle (3) into a hot vapor stream (1, 2) and is vaporized (4). Upon introduction into the hot air stream the droplets are cooled down due to the evaporation of water or a chemical solvent from the concentrate. Solid particles form, while moisture quickly leaves the droplets. In the example illustrated in FIG. 3, a nozzle is used in order to achieve a sufficiently small droplet size (atomizer) and in order to maximize heat transfer and the rate of water/solvent evaporation. A co-current flow of hot drying gas is used in the exemplary device shown in FIG. 3. Particles are further dried and separated in a cyclone device (6). The dry particles are cooled and collected, ready for packaging in different formats (8).

The final product is collected as described above and is preferably in the form of a dry powder comprising the particles as defined herein with respect to the inventive dry powder composition.

The spray-drying process, in the context of the present invention, may be carried out using any suitable spray-drying device known in the art. Examples of commercially available devices that may be employed include, but are not limited to the following examples: Mini Spray Dryer B-290 (Buchi); Nano Spray Dryer B-90 (Buchi); Anhydro MicraSpray Dryer GMP (SPX.com); Anhydro MicraSpray Dryer Aseptic series (SPX.com); MDL-50 series; B,C,S,M sub-types. (fujisaki electric); MDL-015 (C) MGC lab-scale. (fujisaki electric); MDL-050 (C) MGC lab-scale. (fujisaki electric); LSD-1500 Mini spray dryer (cndryer.com); MSD-8 Multi-functional laboratory spray dryer (cndryer.com); PSD-12 Precision pharmacy spray dryer (cndryer.com); PSD-12 Precision pharmacy spray dryer (cndryer.com); TALL FORM DRYER™—TFD (GEA Process Engineering); COMPACT DRYER™—CD (GEA Process Engineering); Multi-Stage Dryer—MSD™ (GEA Process Engineering); FILTERMAT™ Spray Dryer—FMD (GEA Process Engineering); SDMICRO™ (GEA Process Engineering), MOBILE MINOR™ (GEA Process Engineering); PRODUCTION MINOR™ (GEA Process Engineering); VERSATILE-SD™ (GEA Process Engineering); FSD™ Fluidized Spray Dryer (GEA Process Engineering); Standard GEA Niro PHARMASD™ spray dryers (GEA Process Engineering); R&D Spray Dryer—SDMICRO™ (GEA Process Engineering).

In the spray-drying process according to the invention, the drying gas may be any suitable gas or mixture of gases, such as air. Preferably, an inert gas is used as drying gas, for example nitrogen, nitrogen-enriched air, helium or argon.

The spray-drying process is influenced to a considerable degree by the temperature of the drying gas. That temperature is typically characterized by two parameters, i.e. the inlet temperature ($T_{inlet}$) and the outlet temperature ($T_{outlet}$). As used herein, the term 'inlet temperature' refers to the drying gas temperature as measured at the drying gas inlet of the drying chamber as described herein. Analogously, the term 'outlet temperature' refers to the drying gas temperature as measured at the drying gas outlet of the drying chamber as described herein.

For heat sensitive material, the inlet temperature is preferably chosen sufficiently high in order to allow rapid and efficient drying, while at the same time avoiding degradation of the material. If heat sensitive material is dried, the residence time of the material in the drying chamber is preferably increased, e.g. by using larger drying chambers, which allows operating at lower temperatures.

In a preferred embodiment, the outlet temperature is at least about 65° C., at least about 66° C., at least about 67° C., at least about 68° C., at least about 69° C., at least about 70° C., at least about 71° C., at least about 72° C., at least about 73° C., at least about 74° C., at least about 75° C., at least about 76° C., at least about 77° C., at least about 78° C., at least about 79° C., at least about 80° C., at least about 85° C., at least about 86° C., at least about 87° C., at least about 88° C., at least about 89° C., at least about 90° C., at least about 91° C., at least about 92° C., at least about 93° C., at least about 94° C., at least about 95° C., at least about 96° C., at least about 97° C., at least about 98° C., at least about 99° C., at least about 100° C., at least about 101° C., at least about 102° C., at least about 103° C., at least about 104° C., at least about 105° C., at least about 106° C., at least about 107° C., at least about 108° C., at least about 109° C., or at least about 110° C.

According to a particularly preferred embodiment, the outlet temperature is at least about 65° C. Alternatively, the outlet temperature is at least about 69° C. More preferably, the outlet temperature is at least about 70° C., most preferably at least about 71° C. or at least about 72° C.

Typically, higher temperatures increase the efficiency of the spray-drying process. The disadvantage of higher temperatures may be, however, an increased risk of degradation depending on the active ingredient or the excipients. Another caveat with spray-drying in general are shear forces that are acting on the liquid to be dried, in particular during atomization. The shear stress is typically expected to be particularly detrimental to larger molecules. Before the present invention, it was therefore altogether unexpected that a long-chain RNA molecule may be dried by spray-drying, while the long-chain RNA molecule's integrity and biological activity is retained notwithstanding the mechanical stress involved in the process. Even more surprisingly, it has been found by the inventors of the present invention that the long-chain RNA molecule is not degraded, even when relatively high temperatures, in particular outlet temperatures, are used. In contrast, the skilled person would have expected that high outlet temperatures ($T_{outlet}$) used in the spray-drying process (for example, $T_{outlet}$>60° C.) would result in degradation of long-chain RNA. This allows the preparation of a particulate, storage-stable form of long-chain RNA, which advantageously has an outstandingly low residual moisture content that allows for long-term storage without degradation.

One particular advantage of the inventive dry powder composition and the inventive method is that a dry powder composition is provided, which can be divided into packages useful for shipping, storage and use as medicament. Furthermore dry powder formation of long-chain RNA represents a cost- and time effective process, which can readily be scaled-up for commercial production. In this context, it is particularly advantageous that spray drying can be carried out as a continuous process. One advantage of a continuous process is that the product produced in one run has the same properties, therefore reducing the amount of required quality controls.

Preferably, the residual moisture content of the dry powder composition obtained by the method according to the invention is as defined above with regard to the inventive dry powder composition.

More preferably, the relative integrity and the biological activity of the long-chain RNA molecule in the dry powder composition obtained by using the inventive method is preferably as defined above for the inventive dry powder composition comprising a long-chain RNA molecule.

The inventive method thus provides long-chain RNA as defined herein in a particulate formulation. In a particularly preferred embodiment, the particles comprised in the dry powder composition obtained by the inventive method are characterized by a size distribution, which is preferably as defined herein for the particles of the inventive dry powder composition. In a particularly preferred embodiment, the product, which is obtained from the method according to the invention, is the inventive dry powder composition as described herein.

In one aspect, the invention concerns a particle, or a plurality of particles, comprising a long-chain RNA molecule, which is preferably obtainable by the inventive method. Furthermore, the invention is directed to a dry powder composition comprising a long-chain RNA molecule, which is obtainable by the inventive method as defined herein.

In a preferred embodiment, the inventive dry powder composition, the particle obtainable by the inventive method or the dry powder composition obtainable by the inventive method are packaged in single dosages after the drying process is completed. Alternatively, the method may further comprise purification or selection steps, for example in order to separate particles of a certain size or shape.

Advantageously, the inventive dry powder composition, the particle obtainable by the inventive method or the dry powder composition obtainable by the inventive method may also be extended at any stage after the production process per se is finished. For instance, an excipient, preferably as described herein, may be added to the inventive dry powder composition or to the product of the inventive method, respectively. In that manner, the product of the inventive method provides considerable flexibility and allows extension of weight/volume (e.g. for better handling) as well as combination with other active ingredients and excipients. For example, a suitable excipient, preferably as defined herein, such as a carbohydrate, may be added, for example inulin, starch or trehalose. Preferably, the excipient, which is added to inventive dry powder composition or to the particles or dry powder composition obtained by the inventive method, is characterized by a low osmolarity.

If the inventive dry powder composition, the particles or the dry powder composition obtainable by the inventive method is used in the manufacture of a pharmaceutical composition, the powder or the particles can easily be further processed to other dosage forms, such as tablets, capsules, granules or the like.

In a further aspect, the present invention provides a pharmaceutical composition, comprising or consisting of the inventive dry powder composition, the particles as obtainable by the inventive method or the dry powder composition obtainable by the inventive method. In a preferred embodiment, the inventive dry powder composition, the particles as obtainable by the inventive method or the dry powder composition obtainable by the inventive method are pharmaceutical compositions. Alternatively, the inventive pharmaceutical composition comprises the inventive dry powder composition, the particles as obtainable by the inventive method or the dry powder composition obtainable by the inventive method and optionally a pharmaceutically acceptable carrier and/or vehicle. The inventive pharmaceutical composition may optionally be supplemented with further components as defined above for the inventive dry powder composition or for the inventive method. The inventive pharmaceutical composition may be prepared as a whole by the inventive method.

As a first ingredient, the inventive pharmaceutical composition comprises the long-chain RNA in particulate form as defined herein. In particular, the first ingredient of the inventive pharmaceutical composition is the inventive dry powder composition, the particles as obtainable by the inventive method or the dry powder composition obtainable by the inventive method, as defined above. Preferably, the long-chain RNA molecule as defined herein represents a pharmaceutically active ingredient of the pharmaceutical composition.

As a second ingredient the inventive pharmaceutical composition may comprise another class of compounds, which may be added to the inventive pharmaceutical composition in this context, may be selected from at least one pharmaceutically active component. A pharmaceutically active component in this context is a compound that has a therapeutic effect against a particular medical indication, preferably cancer diseases, autoimmune disease, allergies, infectious diseases or a further disease as defined herein. Such compounds include, without implying any limitation, preferably compounds including, without implying any limitation, peptides or proteins (e.g. as defined herein), nucleic acid molecules, (therapeutically active) low molecular weight organic or inorganic compounds (molecular weight less than 5,000, preferably less than 1,000), sugars, antigens or antibodies (e.g. as defined herein), therapeutic agents already known in the prior art, antigenic cells, antigenic cellular fragments, cellular fractions; modified, attenuated or de-activated (e.g. chemically or by irridation) pathogens (virus, bacteria etc.), etc.

Furthermore, the inventive pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive pharmaceutical composition, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred aspect, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred aspect, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person and may be as defined above.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the dry powder composition or the particles as defined herein in such a manner that no interaction occurs, which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds, which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The inventive pharmaceutical composition may be administered orally, parenterally, by inhalation, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intraarticular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the dry powder composition or the particles, as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the components as defined above suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

In a particularly preferred embodiment, the inventive pharmaceutical composition, preferably as an aerosolizable formulation, is for mucosal, intranasal, inhalation or pulmonary delivery. In a preferred embodiment, the pharmaceutical composition comprises the powder or the particles, preferably as defined herein, which are respirable, i.e. which can readily be dispersed in air or in a gas (e.g. by using an inhalation device) and inhaled by a subject. Preferably, the particles of the pharmaceutical composition are as defined herein with respect to the inventive dry powder composition so that at least a portion of the aerosolized particles reaches the lungs. In a preferred embodiment, the pharmaceutical composition according to the invention comprises the inventive dry powder composition, wherein the dry powder composition comprises particles that have a MMAD of 10 μm or less.

The inventive pharmaceutical composition typically comprises a "safe and effective amount" of the components of the inventive pharmaceutical composition as defined above, particularly of long-chain RNA molecule as comprised in the inventive dry powder composition or in the particles obtainable by the inventive method. As used herein, a "safe and effective amount" means an amount of the long-chain RNA molecule that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the long-chain RNA molecule will furthermore vary in connection with the particular condition to be treated and also with the age and physical condition of the patient to be treated, the body weight, general health, sex, diet, time of administration, rate of excretion, drug combination, the activity of the specific (lyophilized) nucleic acid (sequence) employed, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

According to a specific aspect, the inventive dry powder composition, the particles or the dry powder composition obtainable by the inventive method or the inventive pharmaceutical composition may be provided as a vaccine. Such an inventive vaccine is typically composed like the inventive pharmaceutical composition, i.e. it contains a long-chain RNA molecule formulated as defined above and optionally a pharmaceutically acceptable carrier and/or vehicle. Further components may be as defined above for the inventive pharmaceutical composition. The inventive vaccine preferably supports at least an innate immune response of the immune system of a patient to be treated. Additionally, the inventive vaccine furthermore may also elicit an adaptive immune response, preferably, if the long-chain RNA molecule of the inventive vaccine encodes any of the antigens (or antibodies) mentioned herein, which elicit an adaptive immune response or any antigen as defined herein is added to the inventive vaccine, which can effectively induce an adaptive immune response.

The inventive vaccine may also comprise a pharmaceutically acceptable carrier, adjuvant, and/or vehicle as defined above for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal/intrapulmonal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines herein may be administered by an intradermal, subcutaneous, or intramuscular route. Inventive vaccines are therefore preferably formulated in liquid (or sometimes in solid, e.g. as an aerosol) form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those, which are suitable for use in lotions, creams, gels and the like. If the inventive vaccine is to be administered orally, tablets, capsules and the like are the preferred unit dose form. The pharmaceutically acceptable carriers for the preparation of unit dose forms, which can be used for oral administration, are well known in the prior art. The choice thereof will depend on secondary considerations such as taste, costs and storability, which are not critical for the purposes of the present invention, and can be made without difficulty by a person skilled in the art.

Further additives which may be included in the inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

According to a specific embodiment, the inventive vaccine may comprise an adjuvant. In this context, an adjuvant may be understood as any compound, which is suitable to initiate or increase an immune response of the innate immune system, i.e. a non-specific immune response. In other terms, when administered, the inventive vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal.

In this context, the adjuvant is preferably selected from compounds, which are known to be immune-stimulating due to their binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The present invention furthermore provides several applications and uses of the inventive dry powder composition, the particles obtainable by the inventive method or the dry powder composition obtainable by the inventive method. According to one aspect, the invention concerns the use of the inventive dry powder composition, the particles obtainable by the inventive method or the dry powder composition obtainable by the inventive method for the preparation of a medicament for the prophylaxis, treatment and/or amelioration of a disorder or a disease, preferably as defined herein.

According to a further aspect, the present invention is directed to the use of the long-chain RNA molecule in particulate form as defined herein in the treatment or prevention of a disease. Further, the invention concerns the use of the inventive dry powder composition, the particles obtainable by the inventive method or the dry powder composition obtainable by the inventive method, in the treatment or the prevention of a disease, preferably as defined herein. In particular, the present invention concerns the first medical use of the inventive dry powder composition, the particles obtainable by the inventive method or the dry powder composition obtainable by the inventive method as a medicament. The medicament may be in the form of a pharmaceutical composition or in the form of a vaccine as a specific form of pharmaceutical compositions. A pharmaceutical composition in the context of the present invention typically comprises or consists of the inventive dry powder composition, the particles obtainable by the inventive method or the dry powder composition obtainable by the inventive method as defined above, optionally further ingredients, preferably as defined above, and optionally a pharmaceutically acceptable carrier and/or vehicle, preferably as defined above.

According to a further aspect, the present invention concerns a method of treating or preventing a disorder or a disease by administering to a subject in need thereof a pharmaceutically effective amount, preferably as defined herein, of the inventive dry powder composition, the inventive pharmaceutical composition, or the inventive vaccine. Preferably, the method is for treating or preventing a disorder or a disease selected from cancer or tumor diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases, neuronal diseases, or any further disease mentioned herein.

According to one further aspect, the present invention is directed to the use of the long-chain RNA molecule in particulate form, preferably in the form of the inventive dry powder composition, the particles obtainable by the inventive method or the dry powder composition obtainable by the inventive method, for the prophylaxis, treatment and/or amelioration of a disease or disorder as defined herein, wherein the disease or disorder is preferably selected from cancer or tumor diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases, neuronal diseases, or any further disease mentioned herein.

According to another aspect, the present invention is directed to the second medical use of the long-chain RNA in particulate form as defined herein, preferably in the form of the inventive dry powder composition, the particles obtainable by the inventive method or the dry powder composition obtainable by the inventive method for the treatment of diseases as defined herein, preferably to the use thereof for the preparation of a medicament for the prophylaxis, treatment and/or amelioration of various diseases as defined herein, preferably selected from cancer or tumor diseases, infectious diseases, preferably (viral, bacterial or protozoological) infectious diseases, autoimmune diseases, allergies or allergic diseases, monogenetic diseases, i.e. (hereditary) diseases, or genetic diseases in general, diseases which have a genetic inherited background and which are typically caused by a single gene defect and are inherited according to Mendel's laws, cardiovascular diseases, neuronal diseases, or any further disease mentioned herein.

The present invention also allows treatment of diseases, which have not been inherited, or which may not be summarized under the above categories. Such diseases may include e.g. the treatment of patients, which are in need of a specific protein factor, e.g. a specific therapeutically active protein as mentioned above. This may e.g. include dialysis patients, e.g. patients, which undergo a (regular) a kidney or renal dialysis, and which may be in need of specific therapeutically active proteins as defined above, e.g. erythropoietin (EPO), etc.

Likewise, diseases in the context of the present invention may include cardiovascular diseases chosen from, without being limited thereto, coronary heart disease, arteriosclerosis, apoplexy and hypertension, etc.

Finally, diseases in the context of the present invention may be chosen from neuronal diseases including e.g. Alzheimer's disease, amyotrophic lateral sclerosis, dystonia, epilepsy, multiple sclerosis and Parkinson's disease etc.

According to a further embodiment, the present invention also provides a kit, particularly as a kit of parts. Such a kit of parts may contain e.g. the inventive dry powder composition, the inventive pharmaceutical composition or the inventive vaccine as defined above, preferably divided into different parts of the kit. As an example, the inventive pharmaceutical composition or the inventive vaccine may be prepared as a kit of parts, e.g. by incorporating into one or more parts of the kit (all or at least some components of) the inventive pharmaceutical composition or the inventive vaccine as described herein (whereby at least the long-chain RNA in particulate form is included), or the inventive dry powder composition as such, as a dry formulation, i.e. devoid of any liquid component, and in at least one further separate part of the kit a solvent and/or a buffer as described herein with respect to the liquid provided in step a) of the inventive method, the inventive pharmaceutical composition or the inventive vaccine or any further solvent and/or buffer as described herein for lyophilization, transfection and/or injection. Alternatively, the inventive pharmaceutical composition or the inventive vaccine may be prepared as a kit of parts, e.g. by incorporating into one or more parts of the kit only the inventive dry powder composition, the particles obtainable by the inventive method, or the dry powder composition obtainable by the inventive method, as described herein, and in at least one further separate part of the kit a solvent and/or a buffer as described herein for the liquid provided in step a) of the inventive method, for the inventive pharmaceutical composition or the inventive vaccine or any further liquid and/or buffer as described herein for lyophilization, transfection and/or injection. Without being limited thereto, further ingredients of the kit may include components as defined above, e.g. (solutions comprising) proteins, amino acids, alcohols, carbohydrates, metals or metal ions, surfactants, polymers or complexing agents, and/or buffers, preferably all as defined above. These further ingredients may be contained in different parts of the kit (or kit of parts). The kit or kit of parts as described above may contain optionally technical instructions with information on the administration and dosage of the inventive composition. Such a kit, preferably kit of parts, may be applied, e.g., for any of the above mentioned applications or uses.

BRIEF DESCRIPTION OF THE FIGURES

The figures shown in the following are merely illustrative and shall describe the present invention in a further way. These figures shall not be construed to limit the present invention thereto.

A: solution or suspension to be dried inlet, B: atomization gas (e.g. nitrogen) inlet, 1: drying gas (e.g. nitrogen) inlet, 2: heating of drying gas, 3: spraying of solution or suspension, 4: drying chamber, 5: part between drying chamber and cyclone, 6: cyclone, 7: drying gas outlet, 8: product collection vessel.

FIG. 2: Sequence of the mRNA used in this study (R2564; SEQ ID NO: 1).

Figure 1:
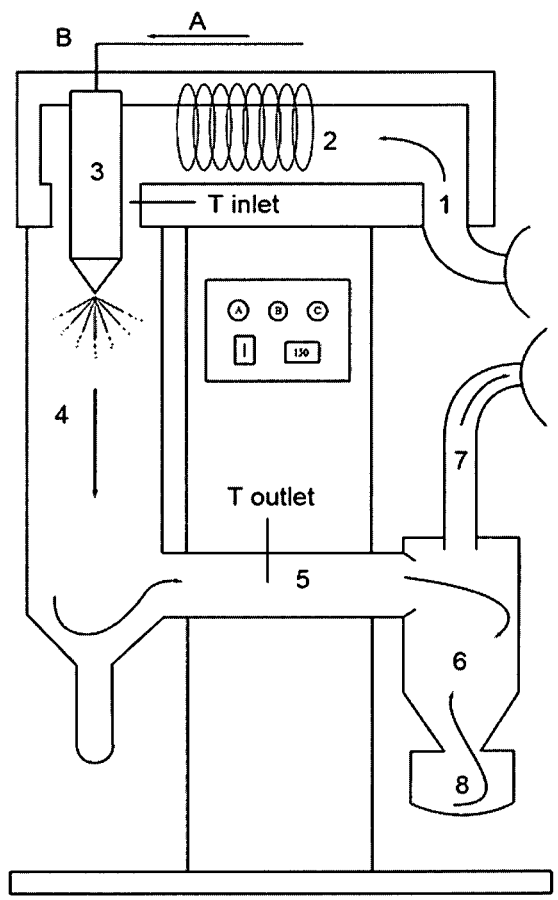
FIG. 1: Scheme of a co-current spray-drying apparatus
Figure 3:
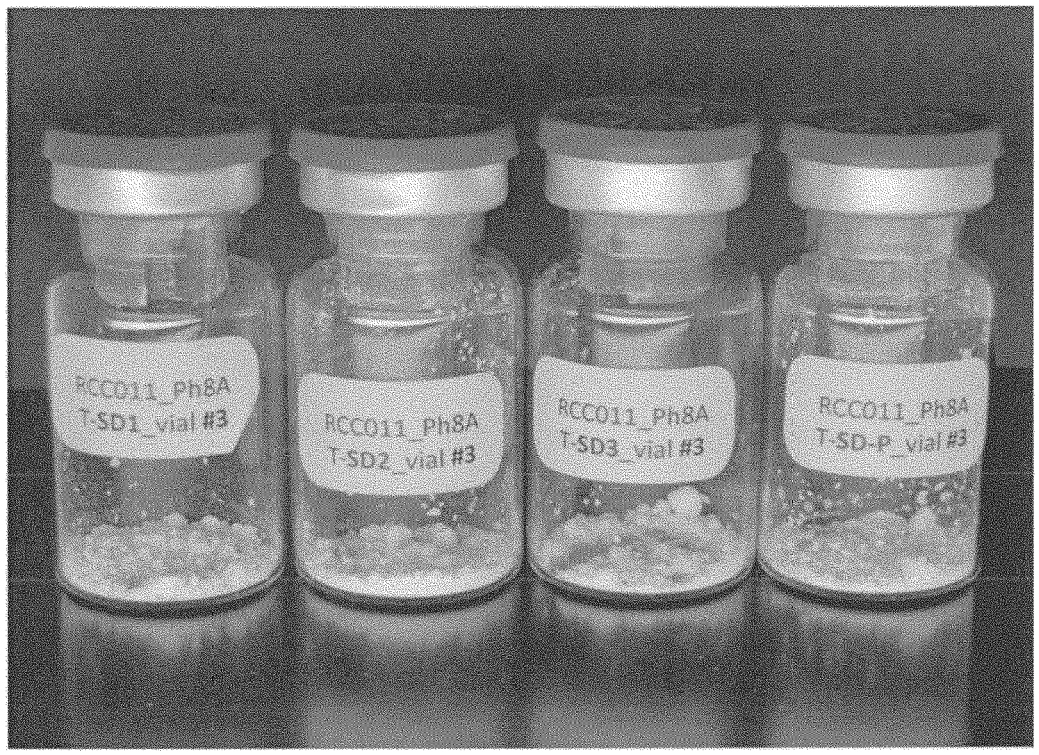

FIG. 3: Photograph of powder of protamine-formulated RNA (T-SD1, T-SD2, T-SD3) spray-dried with outlet temperatures of 47, 69 and 87° C. respectively and of placebo sample (T-SD-P) spray-dried at 84° C.

Figure 4:
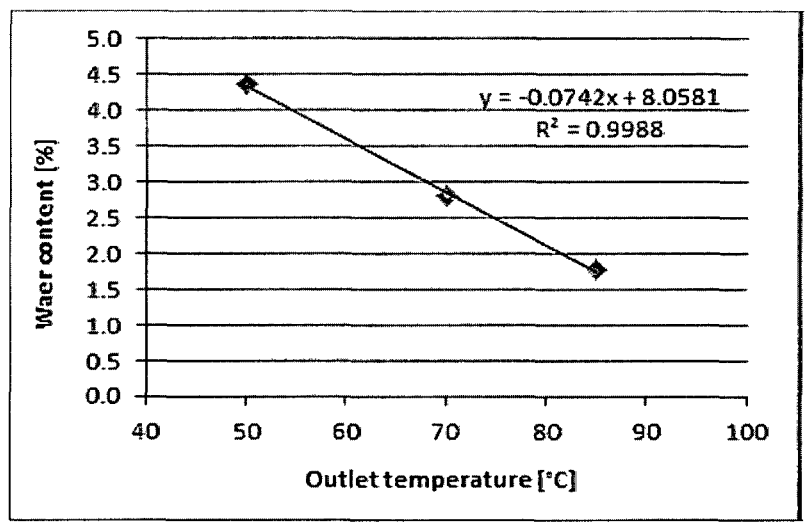

FIG. 4: Residual water content of dry powder formulations obtained by spray-drying using different outlet temperatures.

Figure 5:
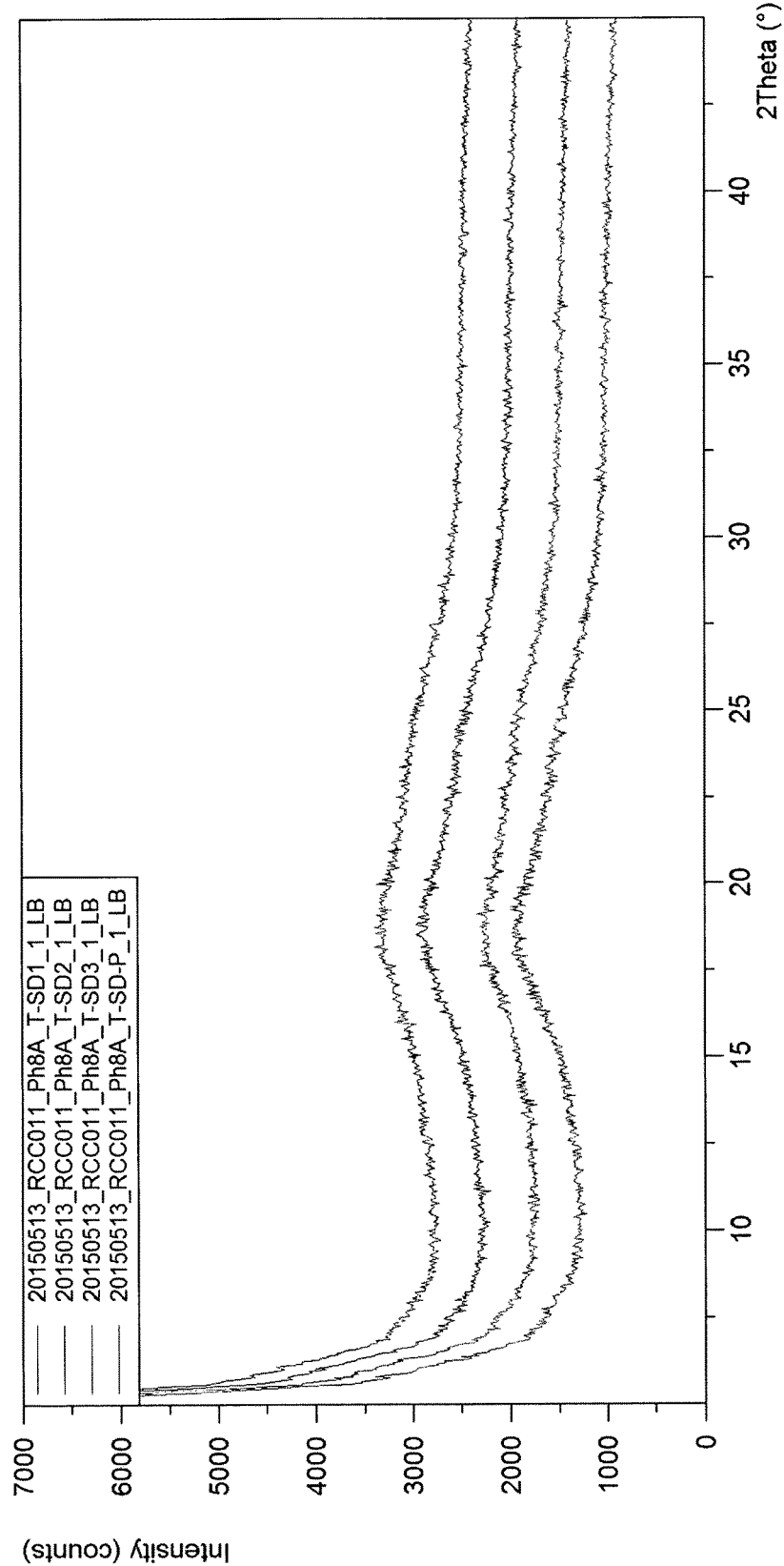

FIG. 5: X-ray powder diffraction analysis of protamine-formulated RNA (T-SD1, T-SD2, T-SD3) spray-dried with outlet temperatures of 47, 69 and 87° C. respectively and placebo sample (T-SD-P) spray-dried at 84° C.

Figure 6:
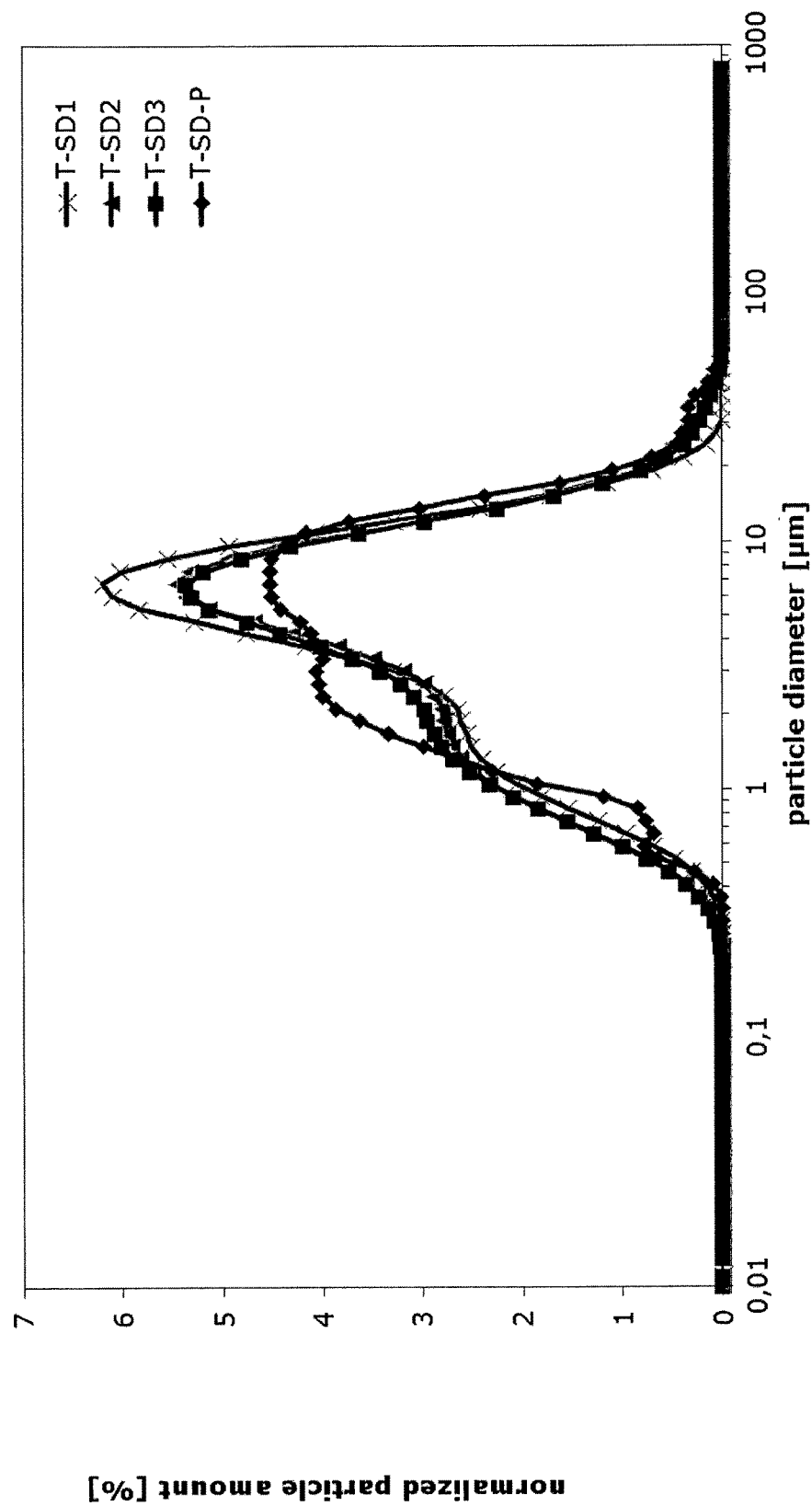
Figure 7A:
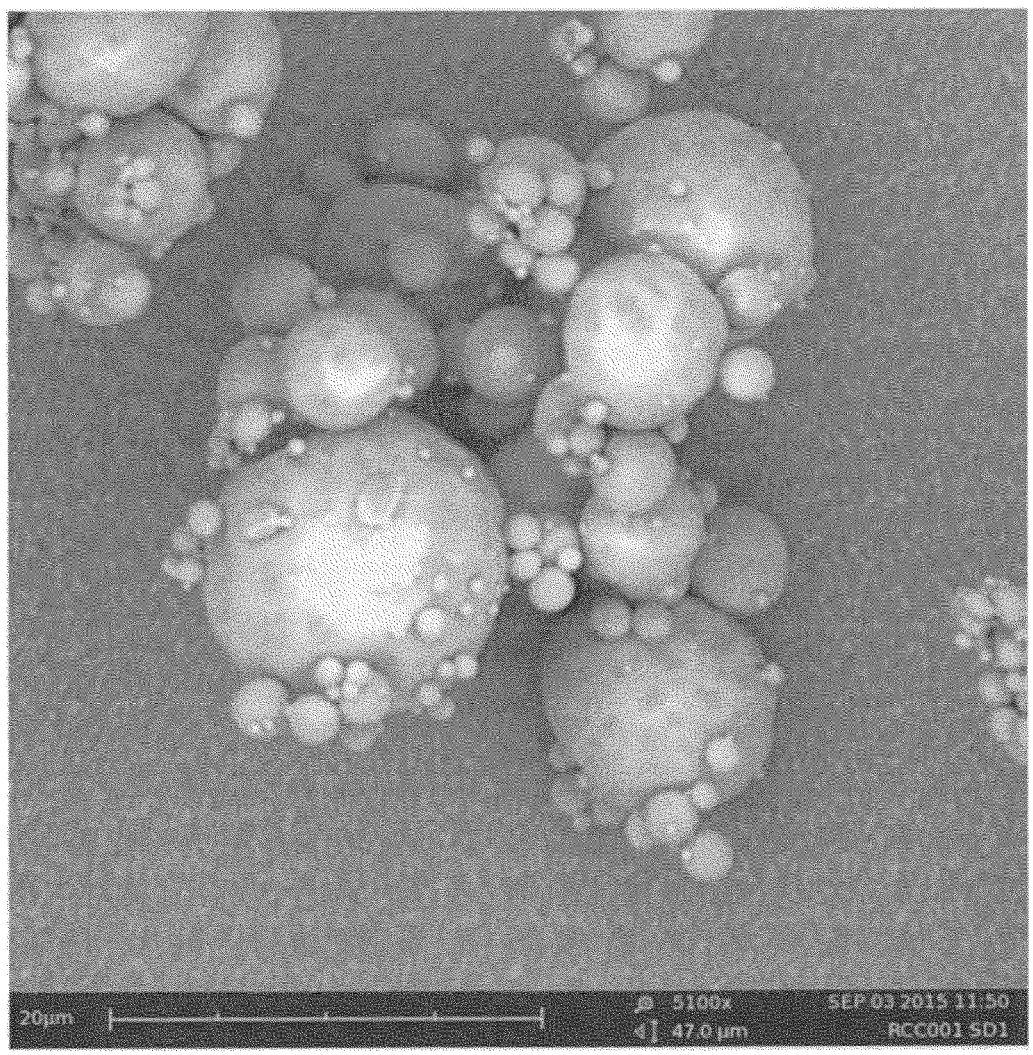
Figure 7B:
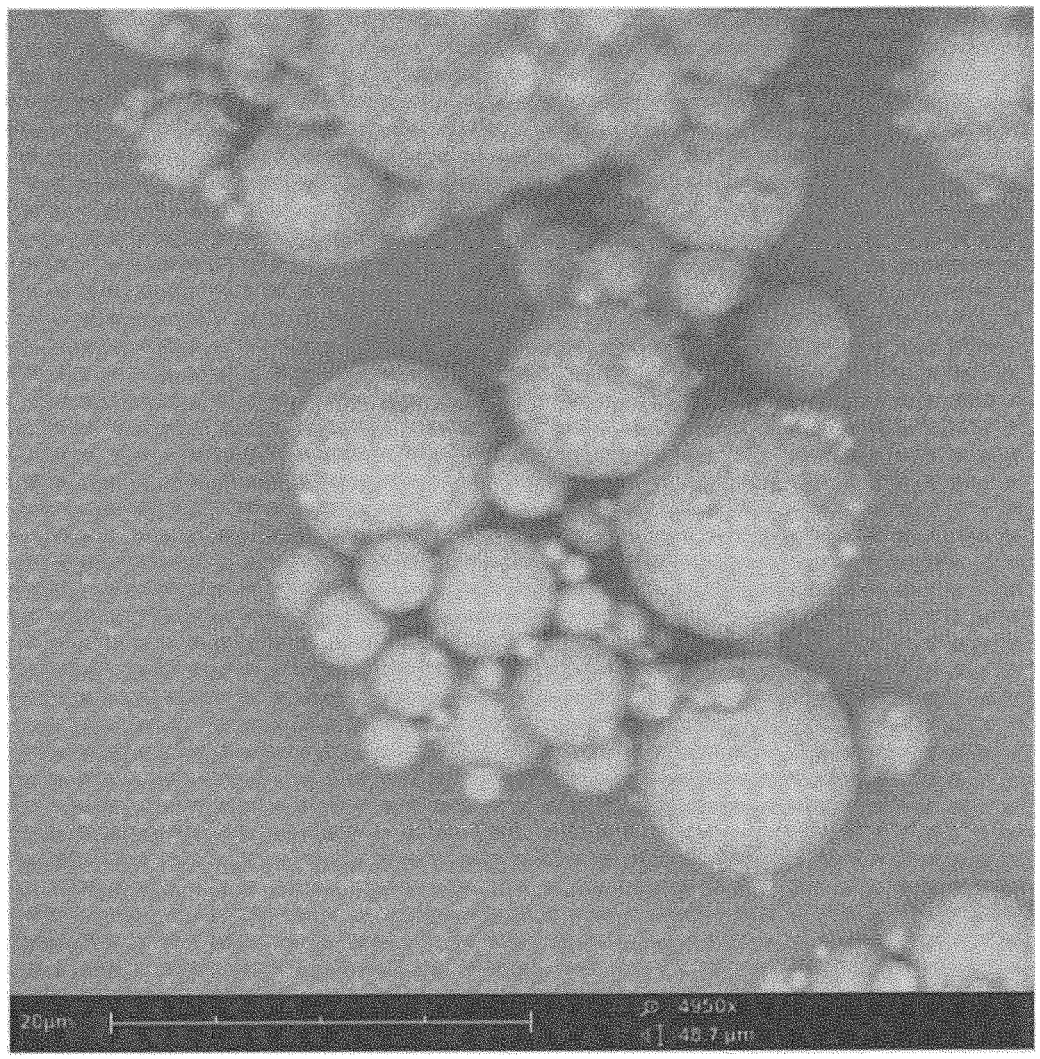
Figure 7C:
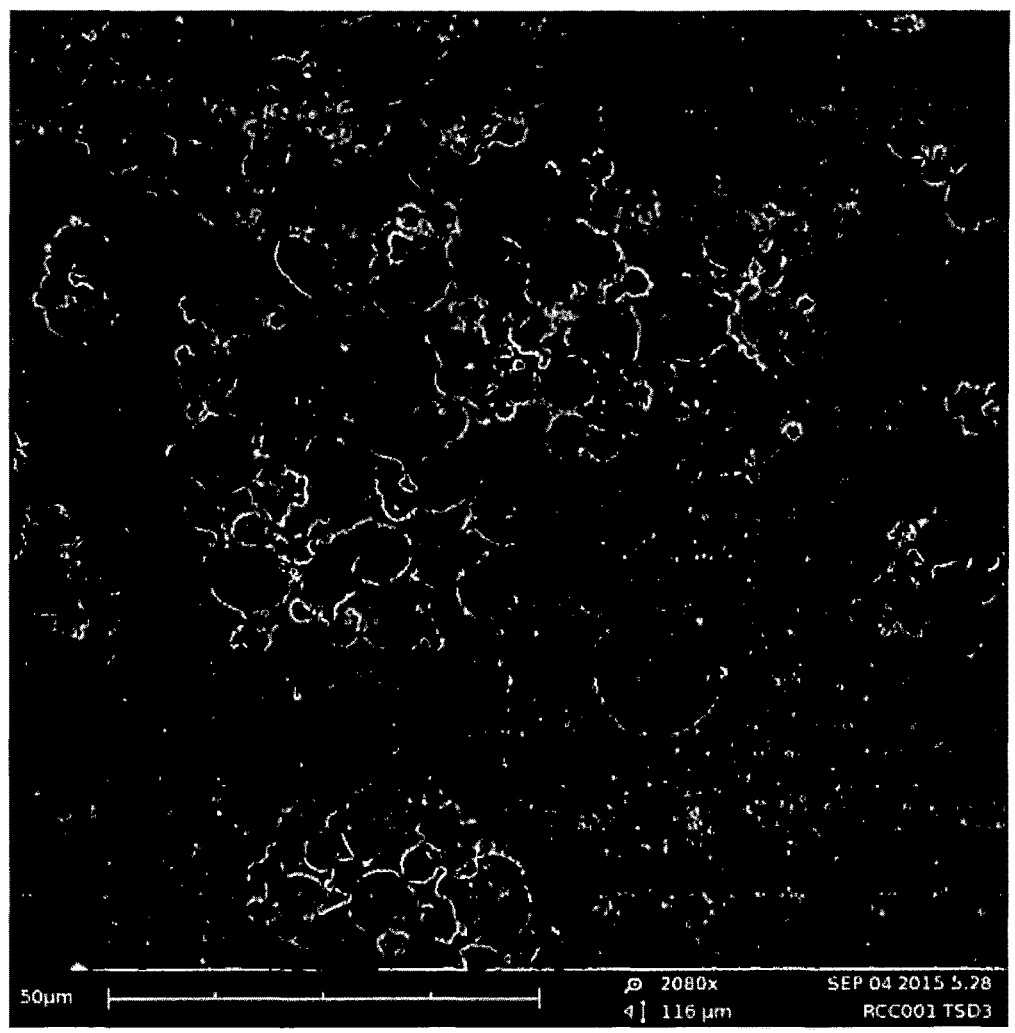
Figure 7D:
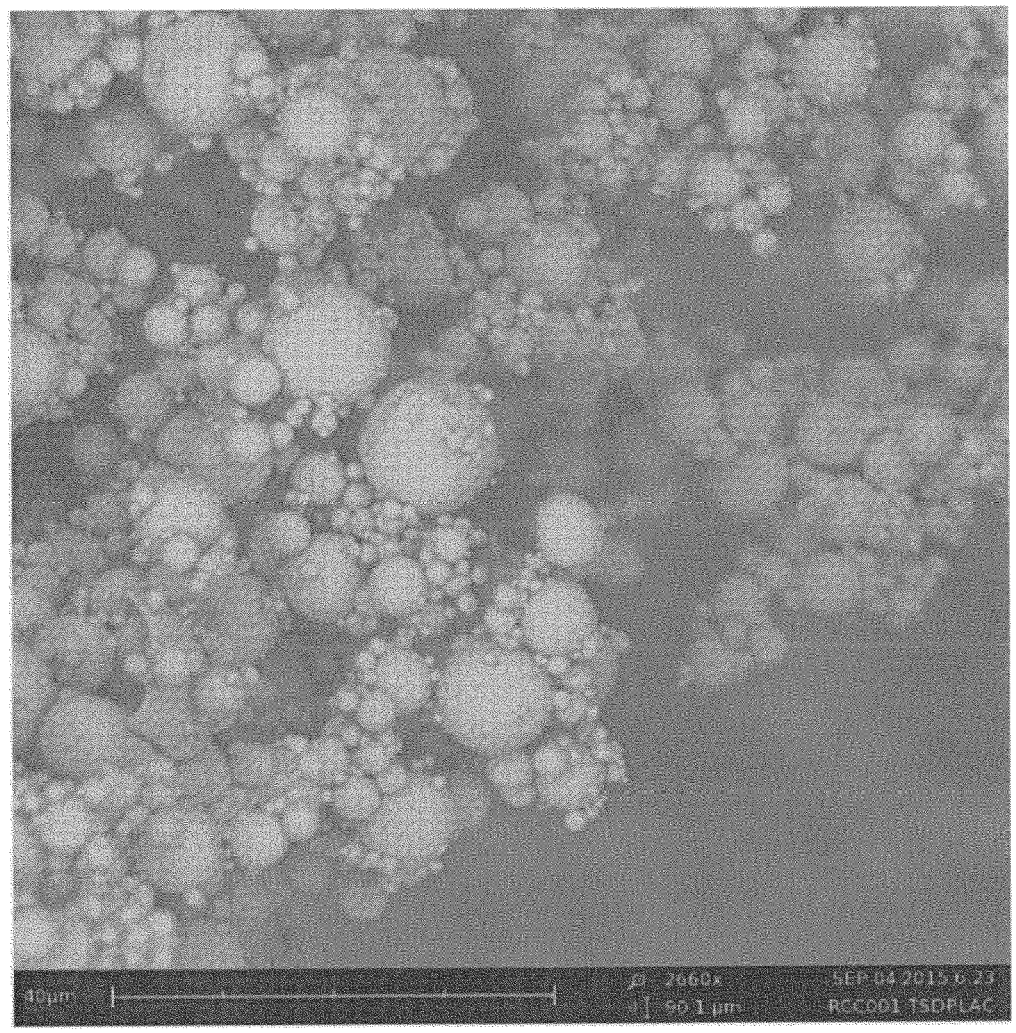

FIG. 6: Particle size distributions of protamine-formulated RNA (T-SD1, T-SD2, T-SD3) spray-dried with outlet temperatures of 47, 69 and 87° C. respectively and placebo sample (T-SD-P) spray-dried at 84° C. as determined by laser diffraction analysis.

FIG. 7: Scanning electron microscope (SEM) images of protamine-formulated RNA powder particles (T-SD-1 (FIG. 7A, 5100×), T-SD-2 (FIG. 7B, 4950×), T-SD-3 (FIG. 7C, 2080×) and placebo powder particles (T-SD-P, FIG. 7D, 2660×).

Figure 8:
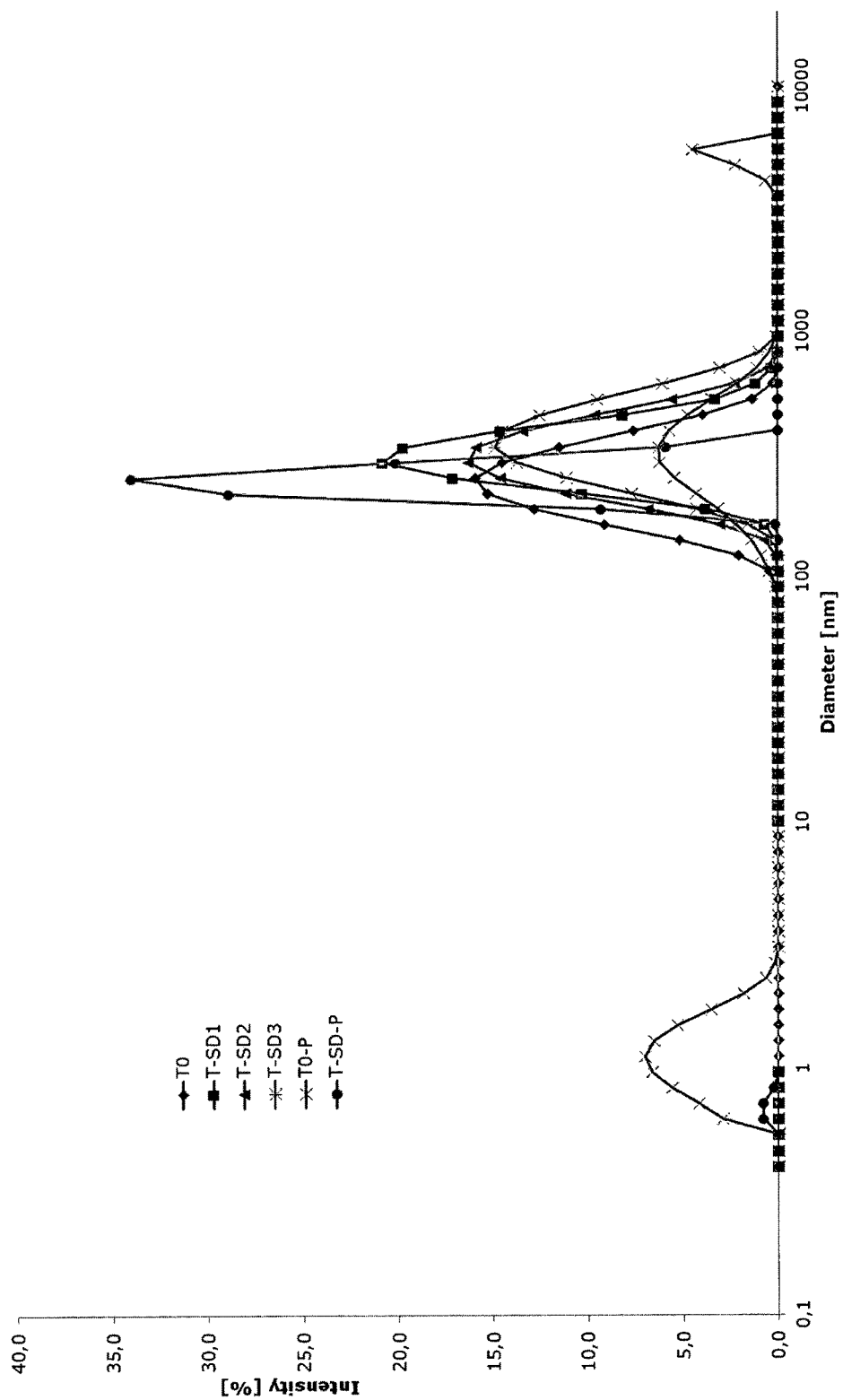

FIG. 8: Particle size distribution of protamine-formulated RNA before (T0) and after (T-SD 1, T-SD 2, T-SD 3) spray-drying with outlet temperatures of 47, 69 and 87° C. respectively and particle size of spray-dried placebo sample (T-SD-P) with an outlet temperature of 84° C. The particle size was determined by dynamic light scattering (DLS).

Figure 9:
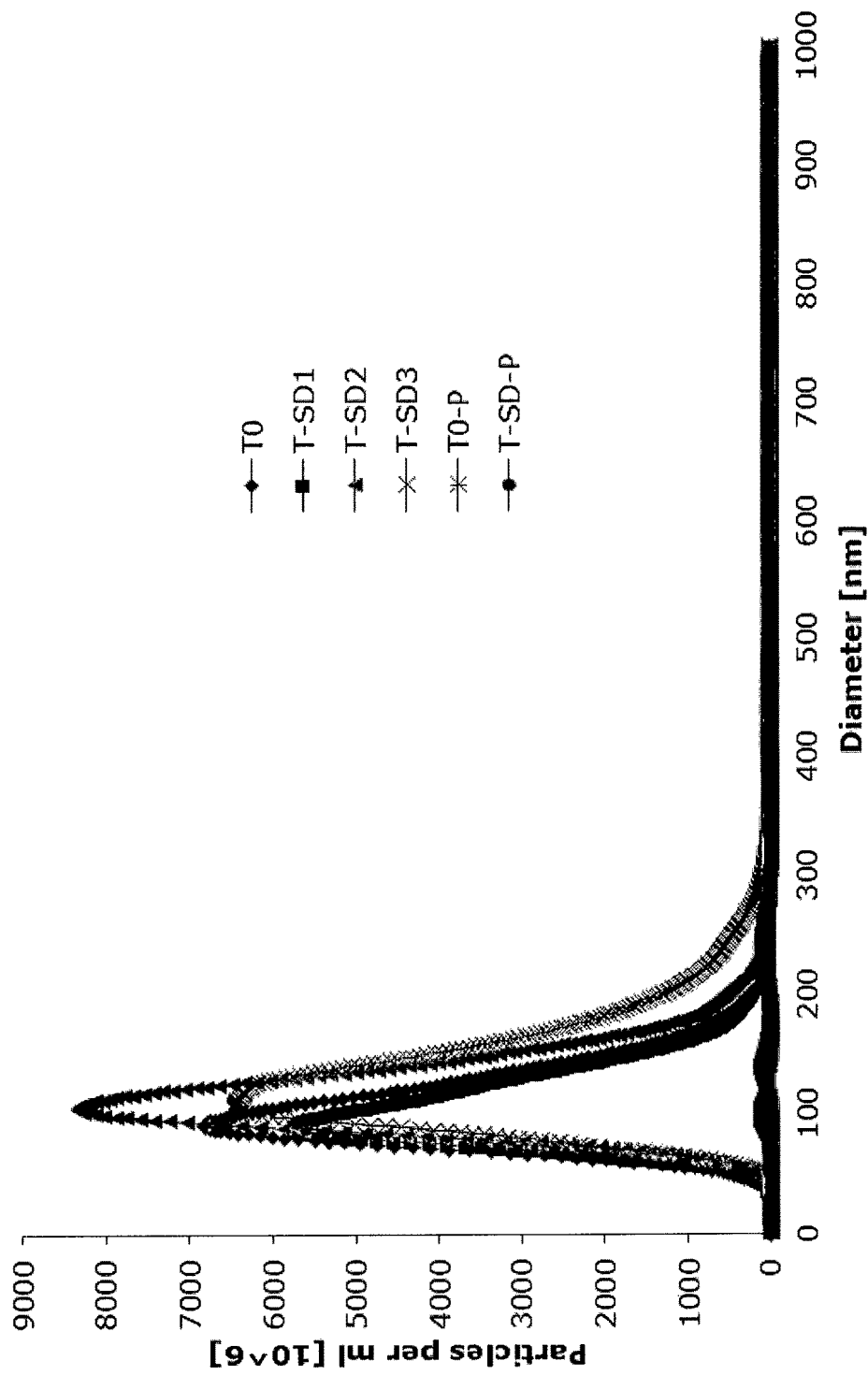

FIG. 9: Particle size distribution of protamine-formulated RNA before (T0) and after (T-SD 1, T-SD 2, T-SD 3) spray-drying with outlet temperatures of 47, 69 and 87° C. respectively and particle size of spray-dried placebo sample (T-SD-P) with an outlet temperature of 84° C. The particle size was determined by nanoparticle tracking analysis (NTA).

EXAMPLES

The Examples shown in the following are merely illustrative and shall describe the present invention in a further way. These Examples shall not be construed to limit the present invention thereto.

Example 1: Preparation of DNA and RNA Constructs

A vector for in vitro transcription was constructed containing a T7 promoter followed by a GC-enriched sequence encoding the hemagglutinin (HA) protein of influenza A virus (A/Netherlands/602/2009(H1N1)) and used for subsequent in vitro transcription reactions. According to a first preparation, the DNA sequence coding for the above mentioned mRNA was prepared. The constructs R2564 (SEQ ID NO: 1) was prepared by introducing a 5'-TOP-UTR derived from the ribosomal protein 32L4, modifying the wild type coding sequence by introducing a GC-optimized sequence for stabilization, followed by a stabilizing sequence derived from the albumin-3'-UTR, a stretch of 64 adenosines (poly (A)-sequence), a stretch of 30 cytosines (poly(C)-sequence), and a histone stem loop. In SEQ ID NO: 1 (see FIG. 2) and the sequence of the corresponding mRNA is shown.

Example 2: In Vitro Transcription and Purification of RNA

The respective DNA plasmids prepared according to section 1 above were transcribed in vitro using T7 polymerase. The in vitro transcription of influenza HA encoding R2564 was performed in the presence of a CAP analog (m7GpppG). Subsequently the RNA was purified using PureMessenger® (CureVac, Tübingen, Germany; WO2008/077592A1).

Example 3: Preparation of Protamine-Formulated RNA

RNA was diluted (0.87 g/L RNA final concentration) and a protamine/trehalose mixture was prepared (43000 anti-heparin IU/L protamine; 10.87% trehalose in water for injection). One volume unit of each solution was mixed to yield a ratio of protamine to RNA of 50 anti-heparin IU per mg RNA.

The solution of RNA/protamine complexes were supplemented with R2564 to yield final concentrations of 0.4 g/L RNA complexed with 20000 anti-heparin IU/L of protamine (corresponding to a protamine concentration of about 1.5 g/L), 0.4 g/L free RNA and 5% trehalose (w/w).

Such formulated RNA was used for spray-drying experiments.

As a placebo, 5% trehalose was prepared in water for injection.

Example 4: Spray-Drying of Protamine-Formulated RNA and Placebo Formulation

The objective of the experiments presented in this section was to test the feasibility of large scale production of the inventive dry powder composition by spray-drying. In summary, three spray-drying experiments were performed at different outlet temperatures using the protamine-formulated RNA prepared according to Example 3. As a control, the placebo formulation as described in Example 3 was processed in parallel.

Protamine-formulated RNA (Example 3) or placebo sample was thawed and each aliquot was homogenized by gentle mixing using a magnetic stirrer before spray-drying.

Spray-drying of protamine-formulated RNA and placebo formulation was carried out using a Büchi Mini Spray-Dryer B-290 equipped with a two-fluid nozzle and a high performance cyclone. The spray-dryer was operated using nitrogen as drying gas in a closed cycle mode. The spray-drying experiments were carried out under the process parameters listed in Table 1.

TABLE 1

| Process parameters spray-drying | | | | |
|---|---|---|---|---|
| Process parameter | T-SD1 (verum) | T-SD2 (verum) | T-SD3 (verum) | T-SP-P |
| Nozzle type | two-fluid nozzle | two-fluid nozzle | two-fluid nozzle | two-fluid nozzle |
| Atomization gas flow setting* (theoretical volume flow) | 30 mm ± 5 mm (~357 l/h) | 30 mm ± 5 mm (~357 l/h) | 30 mm ± 5 mm (~357 l/h) | 30 mm ± 5 mm (~357 l/h) |
| Inlet temperature | 65° C. | 100° C. | 128° C. | 128° C. |
| Outlet temperature | 47° C. | 69° C. | 87° C. | 84° C. |
| Drying gas | nitrogen | nitrogen | nitrogen | nitrogen |
| Drying gas rate/aspirator | 100% (~35 $m^3/h$) | 100% (~35 $m^3/h$) | 100% (~35 $m^3/h$) | 100% (~35 $m^3/h$) |
| Pump speed | 3% (~1 ml/min) | 3% (~1 ml/min) | 3% (~1 ml/min) | 3% (~1 ml/min) |
| Yield [g] | 0.788 | 0.915 | 1.017 | 0.909* |
| Calculated relative yield [%] | 44.2 | 51.4 | 56.5 | 48.3* |

*Atomization gas flow setting of 30 mm correlates with a pressure drop at the nozzle of 0.23 bar Following spray-drying, the produced powders were filled into vials (see section 5) and characterized (see section 6).

5. Powder Filling

The powder obtained after spray-drying was collected in a glass container at the product outlet of the cyclone. For storage, shipment and further analysis the powder was divided into aliquots and transferred into 10R vials under controlled humidity conditions (<15% RH) in a glove box. Vials were stoppered inside the glove box. The exact weight of the dry powder was documented during filling. FIG. 3 shows a photograph of glass vials containing the spray-dried powder.

6. Analytical Characterization

A sampling scheme, including the sampling time points and analytical methods is shown in Table 2.

TABLE 2

| sampling time points for samples from spray-drying | | |
|---|---|---|
| Time point | Description | analytical methods |
| T0 (verum) | Liquid verum sample before spray-drying. | DLS, NTA, MFI, turbidity, ZP |
| T0-P | Liquid placebo formulation before spray-drying | DLS, NTA, MFI, turbidity |
| T-SDX | Spray-dried verum sample obtained from experiment T-SD1, T-SD2, T-SD3, T-SD4 | DLS, ZP, NTA, MFI, turbidity Karl-Fischer titration, DSC, XRD, laser diffraction analysis, SEM |

TABLE 2-continued sampling time points for samples from spray-drying

| Time point | Description | analytical methods |
|---|---|---|
| T-SD-P | Spray-dried placebo sample obtained from experiment T-SD-P | DLS, NTA, MFI, turbidity |

6.1 Methods for Physico-Chemical Characterization of Spray-Dried Powder

Spray-dried powders were characterized with respect to physico-chemical properties of the spray-dried formulation using various methods (Table 3).

TABLE 3

Analytical methods for physico-chemical characterization of spray-dried powder.

| Sample | Abbreviation | Full term |
|---|---|---|
| Dry powder | DSC | Differential scanning calorimetry |
| | KF | Karl Fischer titration |
| | XRD | X-ray powder diffraction |
| | Laser diffraction | Laser diffraction analysis |
| | SEM | Scanning electron microscopy |

6.1.1 Karl Fischer Titration

The residual moisture content of the dried powders were determined using the coulometric Karl Fischer titrator Aqua 40.00 (Analytik Jena GmbH, Jena, Germany), which is equipped with a headspace module.

As a system suitability check, the residual moisture content of a Pure Water Standard (Apura 1 water standard oven 1.0, Merck KGaA) was analyzed prior to sample measurement. The residual moisture content of the standard had to be within 1.00±0.03% in order to comply with the manufacturer specifications.

For the measurement, about 20 mg of sample were weighed into 2R glass vials and heated to a measurement temperature of 120° C. in the oven connected to the reaction vessel via a tubing system. The evaporated water was transferred into the titration solution and the amount of water was determined. The measurement was performed until no more water evaporation was detectable (actual drift comparable to drift at the beginning of the measurement). Ambient moisture was determined by measurement of three blanks (empty vials prepared in the preparation environment). Results obtained for samples were corrected for the determined ambient moisture by blank subtraction. Samples were measured in duplicates. The results are shown in FIG. 4 and Table 4.

TABLE 4

Water content of spray-dried formulation

| Sample | Water content [%] |
|---|---|
| T-SD1 | 4.37 |
| T-SD2 | 2.81 |
| T-SD3 | 1.78 |
| T-SD-P | 1.70 |

6.1.2 Differential Scanning Calorimetry (DSC)

Differential scanning calorimetry (DSC) in a Mettler Toledo 821e (Mettler Toledo, Giessen, Germany) was used to determine thermal events of the spray-dried samples (e.g. glass transition temperature (Tg), crystallization or endothermal melting). Approximately 10 mg of the spray-dried samples were analyzed in crimped Al-crucibles (Mettler Toledo, Giessen, Germany). The samples were cooled to 0° C. at a cooling rate of 10 K/min and reheated to 120° C. with a rate of 10 K/min. The measurement of the temperature profile was repeated in a second cycle in order to evaluate reversibility of thermal events. The Tg was determined as the midpoint of the endothermic shift of the baseline during the heating scan (see Table 5). The maximum of exothermic/endothermic peaks were reported as Tcryst/Tm.

TABLE 5

Tg values of spray-dried formulation

| Sample | Tg ($1^{st}$ scan) [° C.] |
|---|---|
| T-SD1 | 59.0 |
| T-SD2 | 72.1 |
| T-SD3 | 87.9 |
| T-SD-P | 87.8 |

Tg values correlate with the water contents of the samples. No relaxation phenomenon (exothermic event) was detectable in spray-dried samples, in contrast to thermograms obtained for lyophilized samples.

6.1.3 X-Ray Powder Diffraction (XRD)

Wide angle X-ray powder diffraction (XRD) was used to study the morphology of lyophilized products. The X-ray diffractometer Empyrean (Panalytical, Almelo, The Netherlands) equipped with a copper anode (45 kV, 40 mA, Kα1 emission at a wavelength of 0.154 nm) and a PIXcel3D detector was used. Approximately 100 mg of the spray-dried samples were analyzed in reflection mode in the angular range from 5-45° 2θ, with a step size of 0.04° 2θ and a counting time of 100 seconds per step. The respective XRD diagrams are shown in FIG. 5.

All samples showed an amorphous pattern and no indication of crystalline phases.

6.1.4 Laser Diffraction Analysis

Size distribution of spray-dried powders were measured by laser diffraction. Laser diffraction measurements were performed using a Partica LA-950 Laser Diffraction Particle Size Distribution Analyzer (Horiba, Kyoto, Japan) equipped with a 605 nm laser diode for detecting particles>500 nm and 405 nm blue light emitting diode (LED) for detecting particles<500 nm. The powder samples were dispersed in Miglyol 812 by ultra sonication for up to 5 min. Prior to measurement, the system was blanked with Miglyol 812. Each sample dispersion was measured 3 times. Measurement results were analyzed using Horiba LA-950 Software.

The results were reported as

D10: particle diameter corresponding to 10% of the cumulative undersize distribution;

D50: particle diameter corresponding to 50% of the cumulative undersize distribution;

D90: particle diameter corresponding to 90% of the cumulative undersize distribution.

The results are summarized in Table 6 and FIG. 6.

TABLE 6

Particle size distribution of spray-dried powders as measured by laser diffraction

| Sample | Absorbance | Median Diameter | Modal Diameter | Mean Value | St. Dev. | D10 | D50 | D90 |
|---|---|---|---|---|---|---|---|---|
| T-SDP | 0.126 | 4.21 | 6.75 | 4.032 | 0.394 | 1.204 | 4.21 | 12.516 |
| T-SD3 | 0.217 | 4.132 | 6.75 | 3.615 | 0.408 | 0.938 | 4.132 | 11.151 |
| T-SD2 | 0.187 | 4.31 | 6.75 | 3.728 | 0.418 | 0.933 | 4.31 | 11.588 |
| T-SD1 | 0.051 | 4.608 | 6.75 | 3.927 | 0.375 | 1.075 | 4.608 | 10.854 |

(sizes are indicated in μm)

6.1.5 Scanning Electron Microscopy (SEM)

Images of spray-dried powder particles were generated by using the bench top scanning electron microscope Phenom (Phenom-World B.V., Eindhoven, Netherlands). The instrument is equipped with a CCD camera and a diaphragm vacuum pump. Each sample was prepared in a glove box under controlled humidity conditions (<20% relative humidity) by using the following method: a small amount of the powder was carefully put on a self-adhesive carbon foil placed on a sample holder. The sample was analyzed under vacuum with a light optical magnification of 24× and 5 kV acceleration voltage. The electron optical magnification was adjusted between 1160× and 1700× and images were made from representative sections of each sample.

The obtained images (see FIG. 7) demonstrate that the obtained powder particles have spherical shape and that the size of the powder particles is in the range from less than 1 μm to approximately 20 μm.

6.2 Reconstitution of Spray-Dried Samples

For reconstitution of the spray-dried samples, the reconstitution volume was calculated for each sample individually based on the amount of powder weighed into the vial. The calculation was based on the method for reconstitution of lyophilized samples (addition of 600 μl water for injection to 30.6 mg powder per vial).

The reconstitution volume for varying amounts of spray-dried powder was calculated according to the following equation:

$$V_{reconst.} = m_{powder} * 1000 \ \mu l / 51 \ mg$$

$V_{reconst.}$: reconstitution volume in ml $m_{powder}$: mass of powder to be reconstituted in mg (based on a theoretical solid content of 51 mg per ml (50 mg/ml trehalose, 0.8 mg/ml RNA (free+complexed), 20 anti-heparin IU/mL protamine))

The spray-dried samples were reconstituted under laminar flow conditions using a procedure comparable to the procedure for the lyophilized product: cap and stopper were removed from the vial and the calculated volume of water for injection was added to the dry powder (into the center of the vial) by using a multipette with 10 ml combitip. The vial was carefully slewed (shaking was avoided), until all powder particles were dissolved. The reconstitution time was measured as the time required in order to achieve full reconstitution of the dry powder after the liquid has been added. The reconstitution behavior was judged, mainly with respect to foaming, and recorded (see Table 7).

TABLE 7

Reconstitution behaviour

| Sample | Reconstitution time [mm:ss] | Foam formation |
|---|---|---|
| T-SD1 | 01:27 | 0 |
| T-SD2 | 01:20 | 0 |
| T-SD3 | 01:37 | 0 |
| T-SD-P | 01:04 | 0 |

In conclusion, reconstitution times for the spray-dried formulations were below 2 minutes. A slightly shorter resolution time was observed for the placebo formulation (T-SD-P).

6.3 Particle Characterization

The particles comprised in liquid samples of the protamine-formulated RNA as described above were characterized before spray-drying, and after reconstitution of the spray-dried samples (Table 8).

TABLE 8

Analytical methods for characterization of liquid samples (before and after spray- drying and reconstitution).

| Sample | Abbreviation | Full term |
|---|---|---|
| Liquid sample | Visual | Visual inspection |
| | DLS | Dynamic light scattering |
| | MFI | Micro-Flow Imaging |
| | Turbidity | Turbidity |
| | NTA | Nanoparticle tracking analysis |
| | ZP | Zeta potential |

6.3.1 Visual Inspection

For visual inspection, the reconstituted vials were inspected for the presence or absence of visible particles under gentle, manual, radial agitation for 5 sec in front of a white background and for 5 sec in front of a black background according to the European Pharmacopoeia. The inspection was performed by two independent examiners. To further classify the particle content, the method described in the "Deutscher Arzneimittel-Codex" (DAC) was used.

The classification can be described as follows:

No particles visible within 5 sec: 0 point

Few particles visible within 5 sec: 1 point

Medium number of particles visible within 5 sec: 2 points

Large number of particles directly visible: 10 points (Particles that were on the limit of being visible as distinct particles (cloudiness, schlieren) were rated with 2 points.)

The results of the visual inspection of the liquid samples are recorded in Table 9.

TABLE 9

Results of visual inspection

| Sample | Score [Exp 1/2] |
|---|---|
| T-SD1 | 2*/2* |
| T-SD2 | 1*/2 |
| T-SD3 | 1/1 |
| T-SD-P | 2*/2* |

*fiber-like particle(s)

As a result, visible particles were observed in all of the analyzed samples. The majority of the observed particles were fiber-like particles that were likely due to a contamination.

6.3.2 Turbidity

The NEPHLA turbidimeter (Dr. Lange, Düsseldorf, Germany), operating at 860 nm and detecting at 90° angle, was used for turbidity measurements. The system was calibrated with formazin as a standard and the results were given in formazin nephelometric units (FNU).

For the measurement, 2.0 ml solution were analyzed in a clean glass cuvette. The turbidity of the individual samples is indicated in Table 10. After analysis, the sample material was used for further analysis (e.g. DLS, MFI, etc.).

TABLE 10

Turbidity of the liquid samples

| Sample | Turbidity [FNU] |
|---|---|
| T0 | 20.1 |
| T-SD1 | 26.1 |
| T-SD2 | 17.7 |
| T-SD3 | 18.0 |
| T-SD-P | 3.5 |

In summary, the turbidity of the spray-dried protamine-formulated RNA after reconstitution varied from 18 to 26 FNU.

6.3.3 Dynamic Light Scattering (DLS)

DLS measurements were carried out by using a Zetasizer Nano Series (Malvern Instruments, Worcestershire, UK) instrument. 150 μl of the sample were analyzed in small volume disposable cuvettes (UVette) by using an automated mode for each sample. As a control (T0), the protamine-formulated RNA before spray-drying was used.

The Malvern Zetasizer Software was used to calculate Z-average diameter, polydispersity index (PDI) and an intensity size distribution (refractive index and viscosity of water was selected in the software). The results are shown in Table 11 and FIG. 8.

TABLE 11

Z-average diameter, polydispersity index, main peak diameter and main peak intensity as determined by Dynamic light scattering

| Sample | Z-average diameter [nm] | PdI | Main peak diameter [nm] | Main peak intensity [%] | Derived Count Rate |
|---|---|---|---|---|---|
| T0 | 218.7 ± 0.5 | 0.183 ± 0.012 | 263.1 ± 3.6 | 100 ± 0 | 55383 ± 219 |
| T-SD1 | 282.9 ± 8.7 | 0.128 ± 0.103 | 325.6 ± 19.4 | 100 ± 0 | 54725 ± 363 |
| T-SD2 | 267.3 ± 4.9 | 0.208 ± 0.021 | 328.3 ± 4.6 | 100 ± 0 | 48428 ± 394 |
| T-SD3 | 292.7 ± 4.9 | 0.252 ± 0.012 | 380.4 ± 3.6 | 100 ± 0 | 39503 ± 42 |
| T-SD-P | 425.2 ± 36.5 | 0.418 ± 0.050 | 252.3 ± 15.3 | 98.3 ± 3.0 | 1989 ± 197 |

As a result, slightly increased Z-average and main peak diameters were determined for spray dried samples.

6.3.4 Nanoparticle Tracking Analysis (NTA)

NTA experiments were carried out with a NanoSight LM20 (NanoSight, Amesbury, UK). The instrument is equipped with a 405 nm blue laser, a sample chamber and a Viton fluoroelastomer O-Ring. The samples were diluted with ultra-pure water in order to achieve suitable concentrations for NTA measurement. After the measurement, all results were normalized to the original concentration.

Samples were loaded into the measurement cell using a 1 ml syringe. The results of the NTA analysis are shown in Table 12 and FIG. 11. Movements of the particles in the samples were recorded as videos for 60 seconds at room temperature using the NTA 2.0 Software. The recorded videos were analyzed with the NTA 2.0 Software.

TABLE 12

Results from NTA analysis

| Sample | Mean size [nm] | Mode size [nm] | D10 size [nm] | D50 size [nm] | D90 size [nm] | Total Concentration [#/ml] |
|---|---|---|---|---|---|---|
| T0 | 108 ± 2 | 96 ± 7 | 71 ± 1 | 102 ± 3 | 150 ± 5 | 4.74 (±0.16) E+11 |
| T-SD1 | 109 ± 6 | 92 ± 9 | 73 ± 5 | 102 ± 9 | 149 ± 5 | 3.96 (±0.89) E+11 |
| T-SD2 | 120 ± 3 | 107 ± 6 | 83 ± 3 | 114 ± 5 | 161 ± 2 | 5.71 (±0.42) E+11 |

TABLE 12-continued

Results from NTA analysis

| Sample | Mean size [nm] | Mode size [nm] | D10 size [nm] | D50 size [nm] | D90 size [nm] | Total Concentration [#/ml] |
|---|---|---|---|---|---|---|
| T-SD3 | 136 ± 5 | 116 ± 10 | 86 ± 4 | 126 ± 3 | 197 ± 13 | 6.04 (±0.59) E+11 |
| T-SD-P | 139 ± 30 | 131 ± 40 | 117 ± 41 | 136 ± 33 | 161 ± 19 | 8.31 (±9.65) E+09 |

The particle size values determined for the spray-dried samples were comparable or slightly increased with respect to the control (T0).

6.3.5 Zeta Potential Measurements

Zeta potential measurements were carried out with a Zetasizer Nano Series instrument (Malvern Instruments, Worcestershire, UK). 750 µl of each formulation were analyzed in disposable folded capillary cells. For each sample, 3 zeta potential measurements consisting of 100 sub-runs were performed and the mean value for zeta potential was calculated. For all samples, a negative zeta potential was determined (see Table 13).

TABLE 13

| Results of Zeta potential measurements | |
|---|---|
| Sample | Zeta potential [mV] |
| T0 | −32.4 |
| T-SD1 | −35.8 |
| T-SD2 | −36.7 |
| T-SD3 | −41.2 |
| T-SD-P | −22.5 |

6.3.6 Micro-Flow Imaging (MFI)

Micro-Flow Imaging measurements were conducted by using a DPA-5200 particle analyzer system (ProteinSimple, Santa Clara, Calif., USA) equipped with a silane coated high resolution 100 µm flow cell. Samples were analyzed undiluted. In case of excess of the MFI concentrations limits (≥2.5 µm: 900,000 particles/ml, ≤5 µm: 400,000 particles/ml and ≤10 µm: 250,000 particles/mil), samples were diluted before analysis by adding ultrapure water (e.g. Milli-Q water).

For the analysis of the liquid samples, a pre-run volume of 0.17 ml was followed by a sample run of 0.26 ml. Approximately 1100 images were taken per sample. Between measurements, the flow cell was cleaned with water and the background illumination was optimized by using ultrapure water. The MFI View System Software (MVSS) version 2-R2-6.1.20.1915 was used to perform the measurements and the MFI View Analysis Suite (MVAS) software version 1.3.0.1007 was used to analyze the data. The particle counts of the diluted samples were normalized to the original concentration. Significantly increased particle concentrations were determined for the spray-dried samples including placebo (see Table 14), pointing towards particle contamination.

TABLE 14

| Particle concentration as determined by MFI | | | | |
|---|---|---|---|---|
| | Particle concentration [#/ml] | | | |
| Sample | ≥1 µm | ≥2 µm | ≥10 µm | ≥25 µm |
| T0 | 12,509 | 4,115 | 203 | 11 |
| T-SD1 | 174,199 | 32,426 | 218 | 4 |
| T-SD2 | 128,351 | 27,151 | 289 | 18 |
| T-SD3 | 139,397 | 28,440 | 225 | 7 |
| T-SD-P | 183,275 | 35,053 | 86 | 0 |

The invention claimed is:

1. A method for preparing a dry powder comprising a long-chain RNA molecule, wherein the method comprises the steps of:
   a) providing a liquid comprising the long-chain RNA molecule,
   b) spray-drying the liquid of step a) with a spray-drying device having a drying gas inlet and a drying gas outlet, wherein the drying gas has a temperature at the inlet of at least 85° C., wherein the drying gas has a temperature at the outlet of at least 50° C.,
   wherein the dry powder has a residual moisture content of 7% (w/w) or less, wherein the long-chain RNA molecule is in a complex with a cationic or polycationic compound, and wherein the long-chain RNA molecule comprises at least 200 nucleotides.

2. The method according to claim 1, wherein the liquid of step a) further comprises at least one excipient selected from a cryoprotectant, a lyoprotectant and a bulking agent.

3. The method according to claim 1, wherein the liquid of step a) does not contain a lipid compound.

4. The method according to claim 1, wherein the liquid of step a) comprises a spray-drying-compatible solvent.

5. The method according to claim 1, wherein the liquid of step a) is atomized and a droplet resulting from the atomization of the liquid is characterized by a mass median aerodynamic diameter of 300 nm to 200 μm.

6. The method according to claim 1, which comprises a plurality of particles.

7. The method according to claim 6, wherein the median particle size in a volume weighted distribution of the resulting dried powder is at least 1 μm.

8. The method according to claim 6, wherein the average sphericity of the particles in the resulting dried powder is in a range from 0.7 to 1.0.

9. The method according to claim 1, wherein the long-chain RNA molecule is present in the form of a free long-chain RNA molecule, or in the form of a complex comprising the long-chain RNA molecule.

10. The method according to claim 1, wherein the long-chain RNA molecule comprises more than 200 nucleotides.

11. The method according to claim 1, wherein the long-chain RNA molecule comprises at least one modification.

12. The method according to claim 1, wherein the liquid of step a) further comprises a suspending agent and/or an osmolality of about 200 mosmol/l to about 400 mosmol/l.

13. The method according to claim 5, wherein at least a first pressure nozzle is used as an atomizer, optionally wherein the pressure is less than about 1 bar.

14. The method according to claim 1, wherein (a) the method is performed on bulk material, or the method is performed continuously, and/or (b) the method is performed in an open cycle device, or the method is performed in closed cycle device.

15. The method of claim 1, wherein the dry powder comprises an average particle size of 1 μm to 20 μm.

* * * * *

UNITED STATES PATENT AND TRADEMARK OFFICE
CERTIFICATE OF CORRECTION

| | |
|---|---|
| PATENT NO. | : 10,517,827 B2 |
| APPLICATION NO. | : 15/575284 |
| DATED | : December 31, 2019 |
| INVENTOR(S) | : Fabian Johannes Eber et al. |

Page 1 of 1

It is certified that error appears in the above-identified patent and that said Letters Patent is hereby corrected as shown below:

On the Title Page

Item (72) Inventors, delete "Stefanie Sewig" and insert --Stefanie SEWING-- therefor.

Signed and Sealed this
Fifth Day of May, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 2083
<212> TYPE: RNA
<213> ORGANISM: Artificial Sequence
<220> FEATURE:
<223> OTHER INFORMATION: R2564

<400> SEQUENCE: 1
ggggcgcugc cuacggaggu ggcagccauc uccuucucgg caucaagcuu accaugaagg     60
ccauccuggu gguccuccug uacaccuucg ccaccgcgaa cgccgacacg cugugcaucg    120
gcuaccacgc caacaacagc accgacaccg uggacaccgu gcucgagaag aacgucacgg    180
ugacccacuc cgugaaccug cuggaggaca agcacaacgg gaagcucugc aagcugcggg    240
gcgucgcccc gcugcaccuc gggaagugca acaucgccgg cuggauccug gggaacccgg    300
agugcgagag ccuguccacc gcgagcuccu ggagcuacau cguggagacc uccagcuccg    360
acaacggcac gugcuacccc ggcgacuuca ucgacuacga ggagcuccgc gagcagcuga    420
```

```
gcuccgugag cuccuucgag cgguucgaga ucuucccaa gaccagcucc uggcccaacc    480
acgacagcaa caagggggguc accgccgccu gcccgcacgc cggcgcgaag uccuucuaca   540
agaaccugau cuggcucgug aagaagggga acagcuaccc caagcuguccu aagagcuaca   600 ucaacgacaa gggcaaggag gugcuggucc ucuggggau ccaccacccc agcaccucg    660 ccgaccagca gagccuguac cagaacgccg acgccuacgu guucgugggc uccagccgcu   720
acuccaagaa guucaagccc gagaucgcca uccggccgaa ggucgcgac caggagggcc    780 ggaugaacua cuacuggacg cuggugagc ccggggacaa gaucaccuuc gaggcgaccg    840
gcaaccucgu gguccccgc uacgccuucg ccauggagcg gaacgccggg agcggcauca    900 ucauccga caccccgug cacgacugca acacgaccug ccagaccccg aagggcgcca    960
ucaacaccag ccugcccuuc cagaacaucc accccaucac gaucgggaag ugccccaagu   1020
acgugaaguc caccaagcug cgccucgcga ccggccugcg gaacgucccg agcauccagu   1080
cccgcgggcu guucggcgcc aucgccgguu ucaucgaggg cggcuggacc gggauggugg   1140
acggcuggua cgguaccac caccagaacg agcagggcag cgguacgcc gccgaccuca    1200 aguccacgca gaacgcgauc gacgagauca ccaacaaggu gaacagcguc aucgagaaga   1260
ugaaccccca guucaccgcc gugggcaagg aguucaacca ccuggagaag cggaucgaga   1320
accugaacaa gaaggucgac gacggcuucc ucgacaucug gacguacaac gccgagcugc    1380
uggugcuccu ggagaacgag cgcacccugg acuaccacga cuccaacgug aagaaccucu   1440
acgagaaggu ccggagccag cugaagaaca acgccaagga gaucgggaac ggcugcuucg   1500
aguucuacca caagugcgac aacaccugca uggaguccgu gaagaacggg accuacgacu   1560
accccaagua cagcgaggag gccaagcuga ccgcgagga gaucgacggc gugaagcucg    1620
aguccacgcg gaucuaccag auccuggcga ucuacagcac cgucgccagc ucccuggugc    1680
ucguggucag ccuggggggcc aucuccuucu ggaugugcag caacggcucc cugcagugcc    1740
gcaucugcau cugaccacua gugcaucaca uuuaaaagca ucucagccua ccaugagaau    1800
aagagaaaga aaaugaagau caauagcuua uucaucucuu uuucuuuuuc guuguguaa    1860 agccaacacc cugucuaaaa aacauaaauu ucuuuaauca uuuugccucu uuucucugug    1920
cuucaauuaa uaaaaaaugg aaagaaccua gaucuaaaaa aaaaaaaaaa aaaaaaaaa    1980 aaaaaaaaaa aaaaaaaaaa aaaaaaaaaa aaaaaaaau gcaucccccc cccccccccc    2040
cccccccccc ccccaaagg cucuuuucag agccaccaga auu                      2083
```